(12) United States Patent
Sung et al.

(10) Patent No.: US 11,340,324 B2
(45) Date of Patent: May 24, 2022

(54) SYSTEMS, METHODS AND MEDIA FOR AUTOMATICALLY SEGMENTING AND DIAGNOSING PROSTATE LESIONS USING MULTI-PARAMETRIC MAGNETIC RESONANCE IMAGING DATA

(71) Applicant: The Regents of the University of California, Oakland, CA (US)

(72) Inventors: Kyung Hyun Sung, Los Angeles, CA (US); Ruiming Cao, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 337 days.

(21) Appl. No.: 16/806,097

(22) Filed: Mar. 2, 2020

(65) Prior Publication Data

US 2020/0278408 A1    Sep. 3, 2020

Related U.S. Application Data

(60) Provisional application No. 62/812,914, filed on Mar. 1, 2019.

(51) Int. Cl.
*G01V 3/00*      (2006.01)
*G01R 33/50*     (2006.01)
(Continued)

(52) U.S. Cl.
CPC ......... *G01R 33/50* (2013.01); *G06K 9/00536* (2013.01); *G06K 9/6256* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| 2016/0196647 A1* | 7/2016 | Madabhushi .... G01R 33/34084 382/131 |
| 2017/0176565 A1  | 6/2017 | Kwak |
| 2018/0240233 A1  | 8/2018 | Kiraly |

FOREIGN PATENT DOCUMENTS

WO    2018156778 A1    8/2018

OTHER PUBLICATIONS

Cao, R. et al., "Joint Prostate Cancer Detection and Gleason Score Prediction in mp-MRI via FocalNet," IEEE Transactions on Medical Imaging, vol. 38, Issue 11, pp. 2496-2506 (Feb. 27, 2019).

(Continued)

*Primary Examiner* — Walter L Lindsay, Jr.
*Assistant Examiner* — Frederick Wenderoth
(74) *Attorney, Agent, or Firm* — Quarles & Brady LLP

(57) ABSTRACT

In accordance with some embodiments, systems, methods, and media for automatically segmenting and diagnosing prostate lesions using multi-parametric magnetic resonance imaging (mp-MRI) data are provided. In some embodiments, the system comprises is programmed to: receive mp-MRI data depicting a prostate, including T2w data and ADC data; provide the T2w data and ADC data as input to first and second input channels of a trained convolutional neural network (CNN); receive, from the trained CNN, output values from output channels indicating which pixels are likely to correspond to a particular class of prostate lesion, the channels corresponding to predicted aggressiveness in order of increasing aggressiveness, identify a prostate lesion in the data based on output values greater than a threshold; predict an aggressiveness based on which channel had values over the threshold; and present an indication that a prostate lesion of the predicted aggressiveness is likely present in the prostate.

22 Claims, 15 Drawing Sheets

(51) Int. Cl.
*G06T 7/00* (2017.01)
*G06K 9/00* (2022.01)
*G06N 3/08* (2006.01)
*G06K 9/62* (2022.01)

(52) U.S. Cl.
CPC .............. *G06N 3/08* (2013.01); *G06T 7/0012* (2013.01); *G06T 2207/10088* (2013.01); *G06T 2207/20081* (2013.01); *G06T 2207/20084* (2013.01); *G06T 2207/30081* (2013.01); *G06T 2207/30096* (2013.01)

(58) Field of Classification Search
USPC ......................................................... 324/309
See application file for complete search history.

(56) References Cited

OTHER PUBLICATIONS

Chen, L-C et al., "Deeplab: Semantic image segmentation with deep convolutional nets, atrous convolution, and fully connected crfs," IEEE Trans. Pattern Anal. Mach. Intell., vol. 40, No. 4, pp. 834-848, 2018.

Cheng, J. et al., "A neural network approach to ordinal regression," in IEEE International Joint Conference on Neural Networks, pp. 1279-1284, IEEE, 2008.

Fehr, D. et al., "Automatic classification of prostate cancer gleason scores from multiparametric magnetic resonance mages," Proc. Natl. Acad. Sci., vol. 112, No. 46, pp. E6265-E6273, 2015.

Gutierrez, P.A., "Ordinal regression methods: survey and experimental study," IEEE Transactions on Knowledge and Data Engineering, vol. 28, No. 1, pp. 127-146, 2016.

Krahenbuhl et al., "Efficient inference in fully connected crfs with Gaussian edge potentials," Advances in neural information processing, pp. 109-117 (2011).

Kwak, JT et al., "Automated prostate cancer detection using t2-weighted and high-b-value diffusion-weighted magnetic resonance imaging," Med. Phys., vol. 42, No. 5, pp. 2368-2378, 2015.

Lemaitre, G. et al., "Computer-aided detection and diagnosis for prostate cancer based on mono and multi-parametric mri: a review," Comput. Biol. Med., vol. 60, pp. 8-31, 2015.

Lin, T.-Y et al., "Focal loss for dense object detection," in Proc. IEEE Int. Conf. Comput. Vis., pp. 2999-3007, IEEE, 2017.

Lin, T.-Y. et al., "Focal loss for dense object detection." IEEE Transactions on Pattern Analysis and Machine Intelligence (vol. 42, Issue: 2, Feb. 1, 2020). First published on Jul. 23, 2018.

Litjens, G. et al., "Computer-aided detection of prostate cancer in mri," IEEE Trans. Med. Imag., vol. 33, No. 5, pp. 1083-1092, 2014.

Long, J et al., "Fully convolutional networks for semantic segmentation," in Proc. IEEE Conf. Comput. Vis. Pattern Recognit., pp. 3431-3440, 2015.

Tsehay, Y. et al., "Biopsy-guided learning with deep convolutional neural networks for prostate cancer detection on multiparametric mri," in Proc. IEEE Int. Symp. Biomed Imag., pp. 642-645, IEEE, 2017.

Vos, P. et al., "Automatic computer-aided detection of prostate cancer based on multiparametric magnetic resonance mage analysis," Phys. Medicine & Biol., vol. 57, No. 6, p. 1527, 2012.

Wang, Z. et al., "Automated detection of clinically significant prostate cancer in mpmri images based on an end-to-end deep neural network," IEEE Trans. Med. Imag., vol. 37, No. 5, pp. 1127-1139, 2018.

\* cited by examiner

GLEASON SCORE ENCODING FOR MULTI-CLASS CNNs.

| LABEL | CLASS | ONE-HOT ENCODING | ORDINAL ENCODING |
|---|---|---|---|
| NON-LESION | 0 | 1 0 0 0 0 0 | 0 0 0 0 0 |
| GS 3+3 | 1 | 0 1 0 0 0 0 | 1 0 0 0 0 |
| GS 3+4 | 2 | 0 0 1 0 0 0 | 1 1 0 0 0 |
| GS 4+3 | 3 | 0 0 0 1 0 0 | 1 1 1 0 0 |
| GS = 8 | 4 | 0 0 0 0 1 0 | 1 1 1 1 0 |
| GS ≥ 9 | 5 | 0 0 0 0 0 1 | 1 1 1 1 1 |

FIG. 5

FALSE POSITIVES PER PATIENT (FP) AT GIVEN LESION DETECTION SENSITIVITY (SEN). AVG±STD.

|  | INDEX LESIONS | | CLINICALLY SIGNIFICANT LESIONS | | ALL LESIONS | |
| --- | --- | --- | --- | --- | --- | --- |
|  | FP@Sen80% | FP@Sen90% | FP@Sen80% | FP@Sen90% | FP@Sen60% | FP@Sen80% |
| U-Net-Mult | 1.194±0.387 | 1.741±0.491 | 1.386±0.363 | 2.150±0.596 | 1.384±0.411 | 3.525±0.412 |
| U-Net-Sing | 1.161±0.373 | 1.613±0.260 | 1.211±0.202 | 1.753±0.550 | 1.287±0.389 | 2.982±0.184 |
| Deeplab | 1.375±0.401 | 2.201±0.637 | 1.454±0.427 | 2.442±0.802 | 1.553±0.459 | 3.698±1.044 |
| FocalNet | 0.610±0.246 | 1.015±0.369 | 0.651±0.149 | 1.130±0.345 | 0.804±0.210 | 2.296±0.608 |

FIG. 10

FALSE POSITIVES PER PATIENT (FP) AT GIVEN LESION DETECTION SENSITIVITY (SEN) FOR EACH SPECIFIC GLEASON SCORE GROUP. AVG ± STD.

|  | GS 3+3 | | GS 3+4 | | GS 4+3 | | GS >8 | |
| --- | --- | --- | --- | --- | --- | --- | --- | --- |
|  | FP@Sen60% | FP@Sen70% | FP@Sen80% | FP@Sen90% | FP@Sen80% | FP@Sen90% | FP@Sen80% | FP@Sen90% |
| U-Net-Mult | 1.651±0.514 | 2.161±0.675 | 1.189±0.316 | 1.735±0.822 | 0.122±0.109 | 0.284±0.258 | 0.042±0.028 | 0.097±0.104 |
| U-Net-Sing | 1.450±0.273 | 1.974±1.135 | 0.860±0.236 | 1.585±1.476 | 0.111±0.096 | 0.230±0.194 | 0.078±0.091 | 0.210±0.143 |
| Deeplab | 1.410±0.806 | 2.458±1.132 | 1.131±0.335 | 1.821±0.500 | 0.273±0.112 | 0.399±0.324 | 0.061±0.020 | 0.244±0.186 |
| FocalNet | 1.211±0.483 | 1.763±0.631 | 0.577±0.180 | 0.899±0.779 | 0.071±0.108 | 0.231±0.143 | 0.035±0.018 | 0.055±0.065 |

FIG. 11

SYSTEMS, METHODS AND MEDIA FOR AUTOMATICALLY SEGMENTING AND DIAGNOSING PROSTATE LESIONS USING MULTI-PARAMETRIC MAGNETIC RESONANCE IMAGING DATA

CROSS-REFERENCE TO RELATED APPLICATIONS

This application is based on, claims the benefit of, and claims priority to U.S. Provisional Application No. 62/812,914, filed Mar. 1, 2019, which is hereby incorporated herein by reference in its entirety for all purposes.

STATEMENT REGARDING FEDERALLY SPONSORED RESEARCH

N/A

BACKGROUND

Diagnosing prostate cancer (sometimes referred to herein as PCa) is challenging, in part, due to difficulty in detecting and distinguishing indolent PCa from potentially clinically significant PCa. For example, a histologically assigned Gleason score (GS) is typically used to assess lesion aggressiveness. In general medical practice, such as GS is generated based on a non-targeted template driven transrectal ultrasound-guided (TRUS) biopsy, which results in underdetection of clinically significant PCa. Recently, 3 Tesla-based multi-parametric MRI (3 T mp-MRI) has been used to provide a powerful combination of anatomical and functional information for PCa diagnosis, and can potentially play a pivotal role in the diagnosis of PCa by reducing unnecessary biopsies and adding treatment options in active surveillance and focal therapy. The core components of mp-MRI include T2-weighted imaging (T2w), diffusion-weighted imaging (DWI), and dynamic contrast-enhanced imaging (DCE-MRI), each of which provides distinct information. Current diagnostic practice for mp-MRI follows the Prostate Imaging Reporting and Data System: Version 2 (PI-RADS v2), which evaluates radiologic findings in a qualitative or semi-quantitative manner. However, PI-RADS v2 has a limited ability to detect and distinguish between indolent and clinically significant PCa, with a wide range of sensitivity and specificity, mainly due to inter-reader variability and suboptimal analysis. For example, to interpret prostate mp-MRI and generate radiologic findings that are qualitative requires a high level of expertise, relying on T2 morphology and non-quantitative assessment of diffusion restriction and lesional enhancement. Thus, radiologic findings in one component of mp-MRI are often more observable than in another component.

Accordingly, new systems, methods, and media for automatically segmenting and diagnosing prostate lesions using multi-parametric magnetic resonance imaging data are desirable.

SUMMARY

In accordance with some embodiments of the disclosed subject matter, systems, methods, and media for automatically segmenting and diagnosing prostate lesions using multi-parametric magnetic resonance imaging data are provided.

In accordance with some embodiments of the disclosed subject matter, a system for automatically detecting and classifying prostate lesions is provided, the system comprising: at least one hardware processor that is programmed to: receive multi-parameter MRI (mp-MRI) data depicting a portion of a subject's prostate, the mp-MRI data comprising a plurality of components, wherein a first component of the plurality of components comprises T2 weighted (T2w) data, and a second component of the plurality of components comprises apparent diffusion coefficient (ADC) data; provide the T2w data as input to a first input channel of a plurality of input channels of a trained convolutional neural network (CNN) classification model, wherein the trained CNN classification model is configured to receive inputs using the plurality of input channels, each of the plurality of input channels corresponding to one of the plurality of components, and provide outputs using a plurality of output channels, each of the plurality of output cannels indicating a likelihood that each pixel of the data provided to the input channels corresponds to a particular class of prostate lesion of a plurality of classes, with each class of the plurality of classes corresponding to a predicted aggressiveness of a prostate lesion in order of increasing aggressiveness, and wherein the trained CNN classification model was trained using labeled mp-MRI data comprising a multiplicity of slices of T2w data, and a respective multiplicity of co-registered ADC data, and a combination of focal loss (FL) and mutual finding loss (MFL); provide the ADC data as input to a second channel of the plurality of channels; receive, from the trained CNN classification model for each of a plurality of pixels of the mp-MRI data, a plurality of output values from the respective plurality of output channels, wherein each of the plurality of output values is indicative of a likelihood that a prostate lesion of at least the level of prostate lesion aggressiveness corresponding to that output channel is present at the pixel; identify a prostate lesion in the mp-MRI data based one or more output values for one or more pixels of the plurality of pixels being greater than a threshold; predict an aggressiveness of the identified prostate lesion based on which output channels had values over the threshold for the particular pixel; and cause an indication that a prostate lesion of the predicted aggressiveness is likely present in the subject's prostate to be presented to a user.

In some embodiments, a first output channel of the plurality of output channels is associated with a first class that corresponds to a Gleason score of 3+3, a second output channel of the plurality of output channels is associated with a second class that corresponds to a Gleason score of 3+4, a third output channel of the plurality of output channels is associated with a third class that corresponds to a Gleason score of 4+3, a fourth output channel of the plurality of output channels is associated with a fourth class that corresponds to a Gleason score of 8, and a fifth output channel of the plurality of output channels is associated with a fifth class that corresponds to a Gleason score of 9 or more.

In some embodiments, the CNN classification model was trained at least in part by: (i) providing a slice of training T2w data as input to the first input channel of the untrained CNN classification model, and a slice of training ADC data corresponding to the T2w data as input to the second input channel of the untrained CNN classification model; (ii) receiving from the untrained CNN, a first set of outputs comprising a value from each output channel for each pixel of the training mp-MRI data based on the data provided as input at (i); (iii) generating, using label information associated with the training mp-MRI data, a plurality of binary masks that are each associated with one of the plurality of classes, each mask indicating which pixels of the training mp-MRI data are non-lesion and which pixels of the training mp-MRI data correspond to a lesion of at least the class associated with the mask; (iv) generating a first loss value using FL based on a comparison of the plurality of masks and the first set of outputs for each pixel of the training mp-MRI data; (v) providing the slice of training T2w data as input to the first channel of the untrained CNN classification model, and blank data as input to the second channel of the untrained CNN classification model; (vi) receiving from the untrained CNN, a second set of outputs comprising a value from each output channel for each pixel of the training mp-MRI data based on the data provided as input at (v); (vii) providing blank data as input to the first channel of the untrained CNN classification model, and the slide of training ADC data as input to the second channel of the untrained CNN classification model; (viii) receiving from the untrained CNN, a third set of outputs comprising a value from each output channel for each pixel of the training mp-MRI data based on the data provided as input at (vii); (ix) selecting, for MFL, between the second set of outputs and the third set of outputs based on which of the second set of outputs and third set of outputs more closely corresponds to the first set of outputs; (x) generating a second loss value based on a distance between the plurality of masks and the differences between the first set of outputs and the selected set of outputs; and (xi) repeating (i) to (x) for the multiplicity of training slices to generate the trained CNN classification model.

In some embodiments, a first mask of the plurality of masks corresponds to the first class, a second mask of the plurality of masks corresponds to the second class, a third mask of the plurality of masks corresponds to the third class, a fourth mask of the plurality of masks corresponds to the fourth class, and a fifth mask of the plurality of masks corresponds to the fifth class.

In some embodiments, the at least one hardware processor that is programmed to: clip the T2w data using a lower threshold corresponding to an intensity of air and an upper threshold corresponding to an intensity of bladder in the T2w data; and normalize the clipped T2w data to a range of [0,1].

In some embodiments, the at least one hardware processor that is programmed to: select a portion of the T2w data centered on the prostate depicted in the mp-MRI data; and convert the selected portion of the T2w data to a size corresponding to an input size of the first input channel.

In some embodiments, the at least one hardware processor that is programmed to: provide the T2w data as input to the first input channel of the trained CNN classification model, and blank data as input to the second channel of the trained CNN; receive, from the trained CNN classification model for each of a plurality of pixels of the mp-MRI data, a second plurality of output values from the respective plurality of output channels; provide blank data as input to the first input channel of the trained CNN classification model, and the ADC data as input to the second channel of the trained CNN; receive, from the trained CNN classification model for each of a plurality of pixels of the mp-MRI data, a third plurality of output values from the respective plurality of output channels; select one of the plurality of components, $I_{Sel}$, to segment based on which of the second plurality of output values and the third plurality of output values minimizes the expression $$I_{Sel} = \arg\min_{c \in \{I_{ADC}, I_{T2w}\}} d(\hat{y} \otimes f_{out}, \hat{y} \otimes f_c),$$

where $I_{T2w}$ is the T2w data, $I_{ADC}$ is the ADC data, $f_{out}$ and $f_c$ are the plurality of outputs and the second plurality of outputs or third plurality of outputs; and segment the selected component $I_{Sel}$ based on an inferred mask $y^*$ that minimized energy E in the expression $E(y^*)=\Sigma_{i=1}^N \phi_u(y^*|I_{ADC}, I_{T2w}) + \Sigma_{i<j}^N \phi_p(y^*_i, y^*_j|I_{Sel})$, where $\phi_u$ is the unary potential from a negative log-likelihood of a CNN predicted probability map, and $\phi_p$ is the pairwise potential from ith and jth pixels in the CNN predicted probability map.

In accordance with some embodiments of the disclosed subject matter, a method for automatically detecting and classifying prostate lesions is provided, the method comprising: receiving multi-parameter MRI (mp-MRI) data depicting a portion of a subject's prostate, the mp-MRI data comprising a plurality of components, wherein a first component of the plurality of components comprises T2 weighted (T2w) data, and a second component of the plurality of components comprises apparent diffusion coefficient (ADC) data; providing the T2w data as input to a first input channel of a plurality of input channels of a trained convolutional neural network (CNN) classification model, wherein the trained CNN classification model is configured to receive inputs using the plurality of input channels, each of the plurality of input channels corresponding to one of the plurality of components, and provide outputs using a plurality of output channels, each of the plurality of output cannels indicating a likelihood that each pixel of the data provided to the input channels corresponds to a particular class of prostate lesion of a plurality of classes, with each class of the plurality of classes corresponding to a predicted aggressiveness of a prostate lesion in order of increasing aggressiveness, and wherein the trained CNN classification model was trained using labeled mp-MRI data comprising a multiplicity of slices of T2w data, and a respective multiplicity of co-registered ADC data, and a combination of focal loss (FL) and mutual finding loss (MFL); providing the ADC data as input to a second channel of the plurality of channels; receiving, from the trained CNN classification model for each of a plurality of pixels of the mp-MRI data, a plurality of output values from the respective plurality of output channels, wherein each of the plurality of output values is indicative of a likelihood that a prostate lesion of at least the level of prostate lesion aggressiveness corresponding to that output channel is present at the pixel; identifying a prostate lesion in the mp-MRI data based one or more output values for one or more pixels of the plurality of pixels being greater than a threshold; predicting an aggressiveness of the identified prostate lesion based on which output channels had values over the threshold for the particular pixel; and causing an indication that a prostate lesion of the predicted aggressiveness is likely present in the subject's prostate to be presented to a user.

In accordance with some embodiments of the disclosed subject matter, a non-transitory computer readable medium containing computer executable instructions that, when executed by a processor, cause the processor to perform a method for automatically detecting and classifying prostate lesions is provided, the method comprising: receiving multi-parameter MRI (mp-MRI) data depicting a portion of a subject's prostate, the mp-MRI data comprising a plurality of components, wherein a first component of the plurality of components comprises T2 weighted (T2w) data, and a second component of the plurality of components comprises apparent diffusion coefficient (ADC) data; providing the T2w data as input to a first input channel of a plurality of input channels of a trained convolutional neural network (CNN) classification model, wherein the trained CNN classification model is configured to receive inputs using the plurality of input channels, each of the plurality of input channels corresponding to one of the plurality of components, and provide outputs using a plurality of output channels, each of the plurality of output cannels indicating a likelihood that each pixel of the data provided to the input channels corresponds to a particular class of prostate lesion of a plurality of classes, with each class of the plurality of classes corresponding to a predicted aggressiveness of a prostate lesion in order of increasing aggressiveness, and wherein the trained CNN classification model was trained using labeled mp-MRI data comprising a multiplicity of slices of T2w data, and a respective multiplicity of co-registered ADC data, and a combination of focal loss (FL) and mutual finding loss (MFL); providing the ADC data as input to a second channel of the plurality of channels; receiving, from the trained CNN classification model for each of a plurality of pixels of the mp-MRI data, a plurality of output values from the respective plurality of output channels, wherein each of the plurality of output values is indicative of a likelihood that a prostate lesion of at least the level of prostate lesion aggressiveness corresponding to that output channel is present at the pixel; identifying a prostate lesion in the mp-MRI data based one or more output values for one or more pixels of the plurality of pixels being greater than a threshold; predicting an aggressiveness of the identified prostate lesion based on which output channels had values over the threshold for the particular pixel; and causing an indication that a prostate lesion of the predicted aggressiveness is likely present in the subject's prostate to be presented to a user.

In accordance with some embodiments of the disclosed subject matter, a system for determining a class of a cancer is provided, the system comprising: at least one hardware processor that is programmed to: receive multi-parameter imaging data depicting a portion of a subject: provide a first subset of the multi-parameter imaging data as input to a first channel of a trained convolutional neural network (CNN); provide a second subset of the multi-parameter imaging data as input to a second channel of the trained CNN; receive, from the trained CNN, a set of output values corresponding to a set of output channels for a plurality of pixels of the multi-parameter imaging data, the set of output channels corresponding to a set of classes of cancer in order of increasing aggressiveness, and each value indicating a likelihood that the pixel depicts cancerous tissue of at least a particular class of cancer corresponding to the output channel from which the value was output; identify a cancer region in the multi-parameter imaging data based on one or more output values for one or more pixels corresponding to the cancer region being greater than a threshold; predict an aggressiveness of the identified cancer region based on which of the output channels had values over the threshold for one or more pixels; and generate a report indicating that the predicted aggressiveness is present in the cancer region.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

The patent or application file contains at least one drawing executed in color. Copies of this patent or patent application publication with color drawing(s) will be provided by the Office upon request and payment of the necessary fee.

FIG. 5 shows an example of a comparison of different techniques for encoding lesion classifications.

FIG. 10 shows a table of example comparisons of false positives per patient produced by various techniques including techniques based on the mechanisms described herein at particular sensitivity levels.

FIG. 11 shows a table of example comparisons of false positives per patient produced by various techniques including techniques based on the mechanisms described herein at particular sensitivity levels for specific classes of lesion.

DETAILED DESCRIPTION

Figure 1:
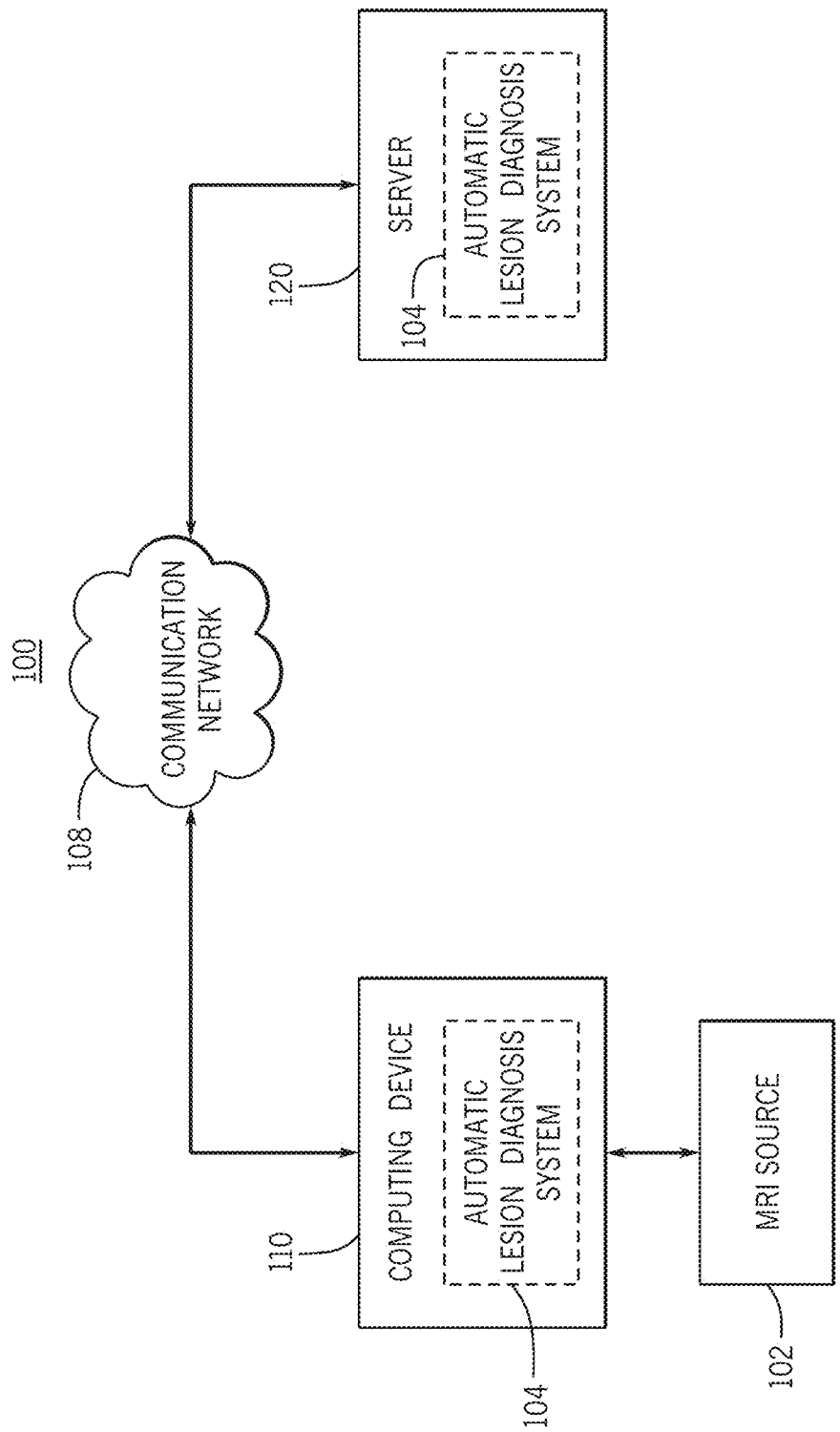
FIG. 1 shows an example of a system for automatically segmenting and diagnosing prostate lesions using mp-MRI data in accordance with some embodiments of the disclosed subject matter.

In accordance with various embodiments, mechanisms (which can, for example, include systems, methods, and media) for automatically segmenting and diagnosing prostate lesions using multi-parametric magnetic resonance imaging (mp-MRI) data are provided.

Computer-aided diagnosis (CAD) using mp-MRI for PCa lesion detection and classification have been attempted. Conventional CAD-based lesion detection approaches have extracted voxel- and/or region-level features from mp-MRI data and attempted to predict PCa localization points or lesion segmentation masks. Recent advances in deep learning have led to convolutional neural networks (CNNs) being incorporated into CAD-based cancer diagnosis using MRI data as a tool for image classification and segmentation. For example, one attempt to incorporate a CNN into a CAD-based approach to cancer diagnosis used hierarchical coarse-to-fine CNNs to segment voxel-level breast cancer tumor masks from dynamic contrast enhanced (DCE)-MRI data and suggest biopsy locations. As another example, a patch-based CNN was used to classify mp-MRI data between biopsy-proven PCa lesion and non-lesion regions of interest (ROIs). As yet another example, a different approach predicts voxel-level labels of clinically significant PCa (i.e., GS>6) and non-clinically-significant PCa (i.e., GS≤6) using a CNN with two output channels to facilitate both detection and classification at the same time.

However, conventional approaches that attempt to utilize multiple components of mp-MRI in CNNs have stacked the different components as different imaging channels (e.g., in place of red, green, and blue channels used by a CNN when analyzing a color image). While this allowed the CNNs to incorporate features that are common across mp-MRI components into the classification model based on labeled groundtruth annotations, it generally fails to incorporate distinct information from each component of mp-MRI. As a result, features that appear in less than all of the components of the mp-MRI data are often not relevant during training of the CNN, especially when the number of training examples is limited.

In some embodiments, mechanisms described herein can use mutual finding loss (MFL) during training to selectively train a CNN across different imaging components of mp-MRI. For example, MFL can be used to identify a subset of components that is likely to contain more observable information for a given PCa diagnosis, and define an object of the lesion-specific training objective to be to detect the PCa finding from the subset of imaging components that is most likely to contain such observable information. Other techniques that have been proposed for using multi-parametric imaging information enforce some level of consistency between different outputs of the imaging components of the mp-MRI data. However, mechanisms described herein that utilize MFL techniques do not need to rely on a strong assumption of the consistency across all imaging components that other proposed techniques rely on. For example, mechanisms described herein that utilize MFL can identify the most distinctive imaging features from one component or multiple (but less than all) component of mp-MRI data to train a CNN (e.g., together with focal loss techniques) for both single and multiple imaging component information at the same time, with minimal changes to the underlying CNN architecture and with no additional parameters to train.

Accurate differentiation between low- and intermediate/high-grade PCa is highly correlated with clinical outcomes, and consequently the ability to accurately stratify clinically significant PCa is desirable. While multi-class classification using CNN has previously been proposed using one-hot encoding techniques, different classes are usually assumed to be equally distanced. However, this assumption ignores the progressiveness of GS groups. For example, in a one-hot encoding scheme the difference between low-grade and intermediate-grade PCa is assumed to be the same as the difference between low-grade and high-grade PCa. In some embodiments, mechanisms described herein can utilize an ordinal encoding scheme to represent different GS groups to incorporate lesion aggressiveness relationships into encoded vectors used to identify each group. Unlike one-hot encoded vectors, ordinal encoded vectors are not mutually orthogonal and can be suggestive of similarities and differences between different GS groups.

Conventional CAD techniques for PCa are generally trained and validated using mp-MRI exams with biopsy-confirmed lesion findings. However, these biopsy-confirmed lesion findings are biased toward lesions that are more easily identified from MRI, since biopsy cores are most often extracted based on MRI-positive findings (e.g., PI-RADS 3). As PI-RADS 3 has a limited ability to detect all PCa lesions, clinically significant lesions can be missed and multi-focal lesions can be highly underestimated using conventional techniques. This can result in an overestimation of the performance of the CAD techniques, because false negatives will be undercounted due to the incompleteness of the information about the prostates depicted in the MRI images used for validation. That is, by considering lesions that were confirmed via a biopsy that was conducted based on a positive identification on an MRI, lesions that are difficult to detect in MRI data will necessarily be underrepresented in the labeled data. Also, there exists a significant risk of inaccurate lesion annotations due to occasional discordance between the GS determined from a prostate biopsy and from a radical prostatectomy specimens. For example, in one review, more than one-third of the biopsy cases with GS 6 were upgraded to GS 7 after examination of the prostate after radical prostatectomy, and one-fourth of GS 3+4 lesions in biopsy were downgraded after examination of the prostate after radical prostatectomy. In some embodiments, mechanisms described herein can use mp-MRI data that was gathered before a robotic-assisted laparoscopic prostatectomy (RALP) was performed. This allows training and validation mp-MRI data to be labeled based on a whole-mount histopathology analysis conducted after RALP, which can provide more accurate definition between the GS groups and can minimize the underestimation of multi-focal lesions and other lesions that are difficult to detect in MRI data.

In some embodiments, mechanisms described herein can be used to train a multi-class CNN to identify PCa lesions in mp-MRI data, and to predict a GS associated with each PCa lesion identified by the CNN in the mp-MRI data. In some embodiments, GS can be organized into five GS groups as follows: GS 3+3, GS 3+4, GS 4+3, GS=8, and GS≥9. In some embodiments, a CNN implemented in accordance with some embodiments of the mechanisms described herein can use six labels, corresponding to five GS groups and normal tissue, to predict a classification of tissues in mp-MRI data. In some embodiments, the six labels can be encoded using an ordinal encoding scheme to encode a particular label as an ordinal vector. In some embodiments, the mechanisms described herein can use a trained CNN to predict a label for each pixel in input mp-MRI data corresponding to a particular portion of a subject's prostate, and can assign an ordinal vector corresponding to the label to that pixel. In some embodiments, a CNN implemented in accordance with some embodiments of the mechanisms described herein can also be trained to select distinctive features in one or certain imaging components of mp-MRI using MFL during the training.

As described below in connection with FIGS. 8-15, the performance of an example implementation of a CNN trained in accordance with some embodiments of the mechanisms described herein was evaluated in comparison with prospective clinical performance of radiologists for lesion detection, and differences in performance were not statistical significance. Radiologists following PI-RADS v2 achieved 83.9% and 80.7% sensitivity for the detection of histopathology-proven index lesions and clinically significant lesions, respectively. The example CNN implemented in accordance with some embodiments of the mechanisms described herein had slightly lower, 80.5% and 79.2% sensitivity at the same false positives per patient, which were not significantly different from the radiologist performance ($p=0.53$ and $p=0.66$), while classifying the data much more quickly than the radiologists (and correspondingly at much lower initial cost per evaluation). The mp-MRI exams used in this evaluation were interpreted and scored by expert genitourinary (GU) radiologists having 10+ years of post-fellowship experience that read more than 1,000 prostate MRI exams yearly. Accordingly, the reported radiologist performance is expected to at least approximate the upper limit of prostate MRI reading quality under the current guideline. As prostate MRI reading quality largely varies according to the reader's experience, the mechanisms described herein can potentially be used to assist less experienced readers and/or augment the PCa detection task for non-experts. Additionally, direct numerical comparisons between the CNN trained in accordance with some embodiments of the mechanisms described herein and the radiologist performance may include some bias due different definitions for true and false detection. For example, true positives for the example CNN implemented in accordance with some embodiments of the mechanisms described herein were defined as localized detection points in or within 5 mm of the lesion ROIs defined based on a whole-mount histopathology analysis, while true positives for the radiologist performance were defined as lesions in the same quadrant and in the appropriate segment. This limitation is mainly due to using PI-RADS as the basis for defining the radiologists task, and PI-RADS being designed for clinical interpretation, not for the specific detection task used in the evaluation of the mechanisms described herein.

Figure 6A:
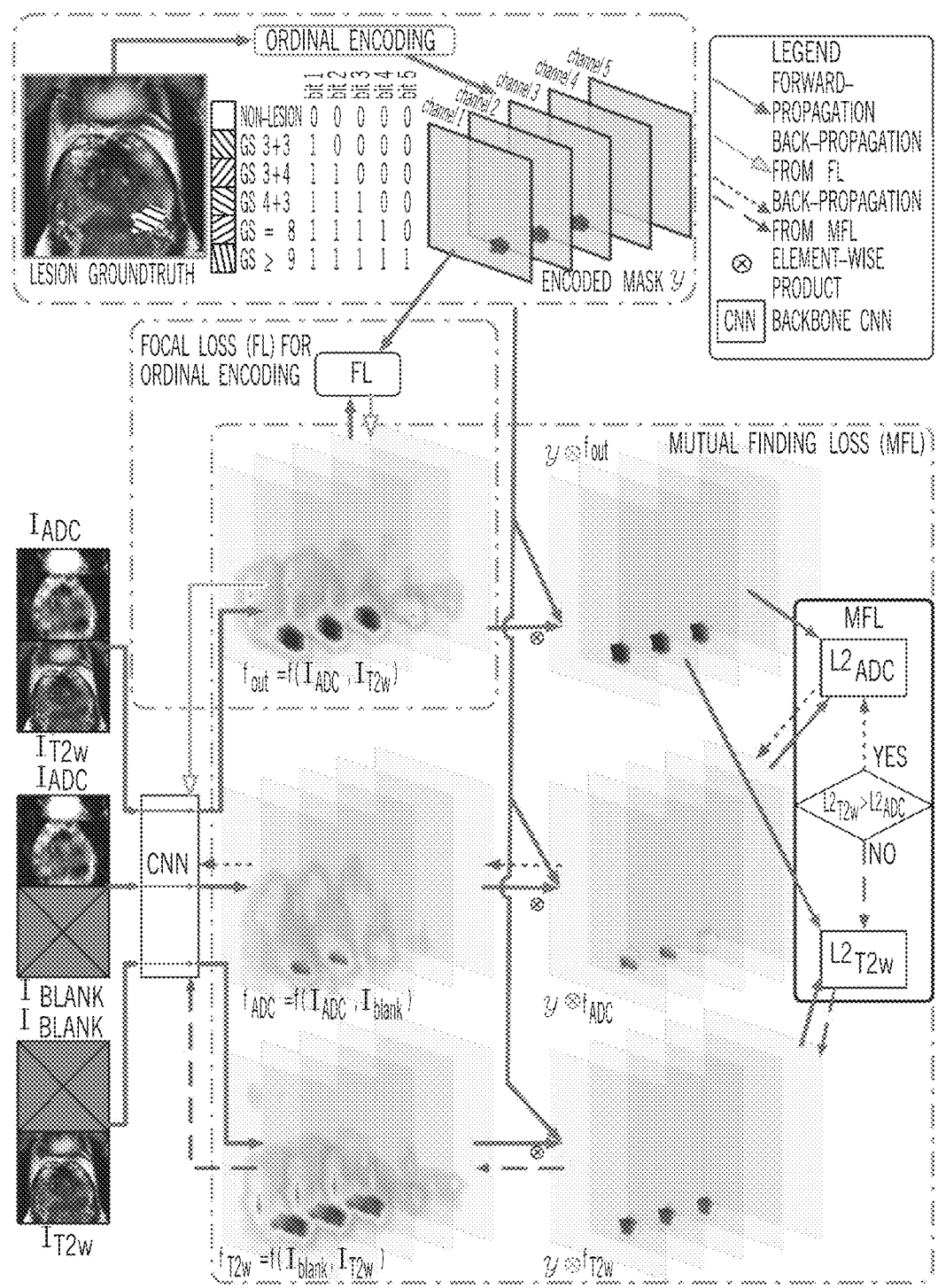
FIG. 6A shows a more particular example of a flow that can be used to train mechanisms for automatically diagnosing prostate lesions using mp-MRI data in accordance with some embodiments of the disclosed subject matter.

Note that mechanisms described herein are described in connection with two imaging components of mp-MRI. However, this is merely an example, and MFL can be extended to additional imaging components, such that where $f_{out}$ is the CNN output with all components, m is the number of imaging component subsets, and $f_i$ is the CNN output using the i-th subset of imaging components. However, each additional imaging component used in by the CNN requires additional GPU memory and adds considerable computation overhead during training, since every imaging component subset requires one forward-propagation of the CNN for the calculation of MFL (e.g., as shown in FIG. 6A). Accordingly, it may be impractical to account for a large number of imaging components given current technological limitations. As such limitations become less pertinent with improved GPU memory and processing power, it may become more practical to use additional components. Additionally or alternatively, pre-determined combinations of imaging components can be used, and these combinations can be considered as possible subsets of imaging components to train with MFL.

In some embodiments, a CNN implemented in accordance with some embodiments of the mechanisms described herein can be adapted for PCa lesion segmentation tasks. For example, the first output channel of such a CNN can predict a classification for each portion of the input data as lesion vs. non-lesion. In some embodiments, additional post-processing techniques such as thresholding, fully-connected conditional random fields, etc., can be applied on the predicted probabilities for lesion segmentation.

Note that mechanisms described herein are described as being implemented using a 2D CNN instead of a 3D CNN for prostate mp-MRI for various reasons. For example, in the protocol used to generate the image data the imaging is non-isotropic. As another example, current 3D PCa lesion annotations are often error-prone due to the difficulty of prostate mp-MRI interpretation. As yet another example, a 3D CNN has more parameters and thus requires more training samples. However, this is merely an example, and the mechanisms described herein are not limited to 2D CNNs. For example, while a 2D CNN may be more appropriate for PCa segmentation and/or classification, 3D CNNs may be more suitable for lesion detection and/or segmentation in other domains (e.g., brain imaging) when the 3D CNN can more fully benefit from the volumetric spatial information available in such a domain. Accordingly, mechanisms described herein for using 2D prostate mp-MRI data to train and use a CNN to automatically segment and diagnose prostate lesions can be used in the context of other types of tissues, and with volumetric (i.e., 3D) data.

In some embodiments, mechanisms described herein can combine voxel-level predictions with a region-level GS classifier. For example, region-level classification models can be used to classify GS for candidate regions provided by the lesion detection output from a CNN implemented in accordance with some embodiments of the mechanisms described herein. Such a hybrid approach can potentially improve the GS classification performance due to region-based classifiers providing additional robustness to pixel-level classifications.

Accurate groundtruth lesion annotation is one of the key challenges for PCa CAD systems. Many studies have used mp-MRI exams with biopsy-confirmed lesion findings to generate groundtruth data, which could potentially include some inaccuracies because of the discrepancy between prostate biopsy and radical prostatectomy (e.g., via a RALP procedure) in histologic findings. Recently, attempts have been made to improve inaccurate lesion annotations by using MR-guided biopsy to generate groundtruth data. While this may reduce the chances of lesion misdetection and GS upgrading/downgrading due to misplacement of the biopsy needle during biopsy, MR-guided biopsy confirmations may still include inaccurate histologic finding and do not provide information of the exact shape, location, and size of the lesions. In some embodiments, lesions can be labeled based on whole-mount histopathology specimens from radical prostatectomy to generate groundtruth data, which can be used to provide more accurate lesion characterizations.

Note that mechanisms described herein did not include MRI non-visible lesions in the groundtruth data used for training and testing because they are difficult to annotate via visual co-registration from whole-mount histopathology, and it is difficult to confirm whether the imaging plane sufficiently contains the lesion information at the time of MRI scan.

FIG. 1 shows an example 100 of a system for automatically segmenting and diagnosing prostate lesions using mp-MRI data in accordance with some embodiments of the disclosed subject matter. As shown in FIG. 1, a computing device 110 can receive multiple types of MRI data from MRI source 102. In some embodiments, computing device 110 can execute at least a portion of an automatic prostate lesion segmentation and diagnosis system 104 (sometimes referred to as automatic lesion diagnosis system 104) to automatically determine whether lesions are present in MRI data of a subject's prostate based on multiple components of the MRI data, such as information from both T2 weighted (T2w) MRI data and apparent diffusion coefficient (ADC) MRI data corresponding to the subject's prostate.

Additionally or alternatively, in some embodiments, computing device 110 can communicate information about MRI data received from MRI source 102 to a server 120 over a communication network 108, which can execute at least a portion of automatic lesion diagnosis system 104 to automatically determine whether prostate lesions are present in mp-MRI data of a subject's prostate based on multiple components of the MRI data, such as information from both T2w MRI data and ADC MRI data corresponding to the subject's prostate. In such embodiments, server 120 can return information to computing device 110 (and/or any other suitable computing device) indicative of an output of automatic lesion diagnosis system 104 to determine whether prostate lesions are present or absent, and information indicative of a predicted aggressiveness of prostate lesions that were identified.

In some embodiments, computing device 110 and/or server 120 can be any suitable computing device or combination of devices, such as a desktop computer, a laptop computer, a smartphone, a tablet computer, a wearable computer, a server computer, a virtual machine being executed by a physical computing device, etc. As described below in connection with FIGS. 3-7, in some embodiments, automatic lesions diagnosis system 104 can classify portions of input mp-MRI data as corresponding to either a lesion or corresponding to normal tissue using a convolutional neural network (CNN) with weights that are initialized based on a general object classification task (e.g., through training using a set of classes of general objects, such as classes of objects included in the ImageNet dataset). For example, one or more transfer learning techniques can be used to train a CNN in which initial weights are based on a pre-trained CNN that has been trained for a general purpose image classification task. Additionally, in some embodiments, automatic lesions diagnosis system 104 can label portions of one or more components of the input mp-MRI data as corresponding to a particular classification (e.g., corresponding to a particular Gleason score) indicative of the predicted aggressiveness of the lesion using the CNN. In some embodiments, during a training phase, mp-MRI data corresponding to a particular subject can be provided to the CNN in various combinations on different input channels, and the CNN can provide output on multiple channels, with each output channel corresponding to a particular class of lesion. In some embodiments, the outputs of the various channels can be compared to labeled masks that indicate which portion(s) of the mp-MRI data correspond to a lesion in the prostate depicted in the mp-MRI data. In some embodiments, the result of comparisons between the labeled masks and the outputs of the various CNN channels can be used to determine which components of mp-MRI data to use to train the CNN. In some embodiments, after training and validation, automatic lesions diagnosis system 104 can provide unlabeled mp-MRI data to the trained CNN, which can provide output indicative of the presence or absence of lesions in different portions of the prostate represented in the mp-MRI data, and an indication of the predicted aggressiveness of any lesions that were identified.

In some embodiments, MRI source 102 can be any suitable source of MRI data, such as an MRI machine, another computing device (e.g., a server storing MRI data), etc. In some embodiments, MRI source 102 can be local to computing device 110. For example, MRI source 102 can be incorporated with computing device 110 (e.g., computing device 110 can be configured as part of a device for capturing and/or storing MRI data). As another example, MRI source 102 can be connected to computing device 110 by a cable, a direct wireless link, etc. Additionally or alternatively, in some embodiments, MRI source 102 can be located locally and/or remotely from computing device 110, and can communicate MRI data to computing device 110 (and/or server 120) via a communication network (e.g., communication network 108).

In some embodiments, communication network 108 can be any suitable communication network or combination of communication networks. For example, communication network 108 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, 5G NR, etc.), a wired network, etc. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 2:
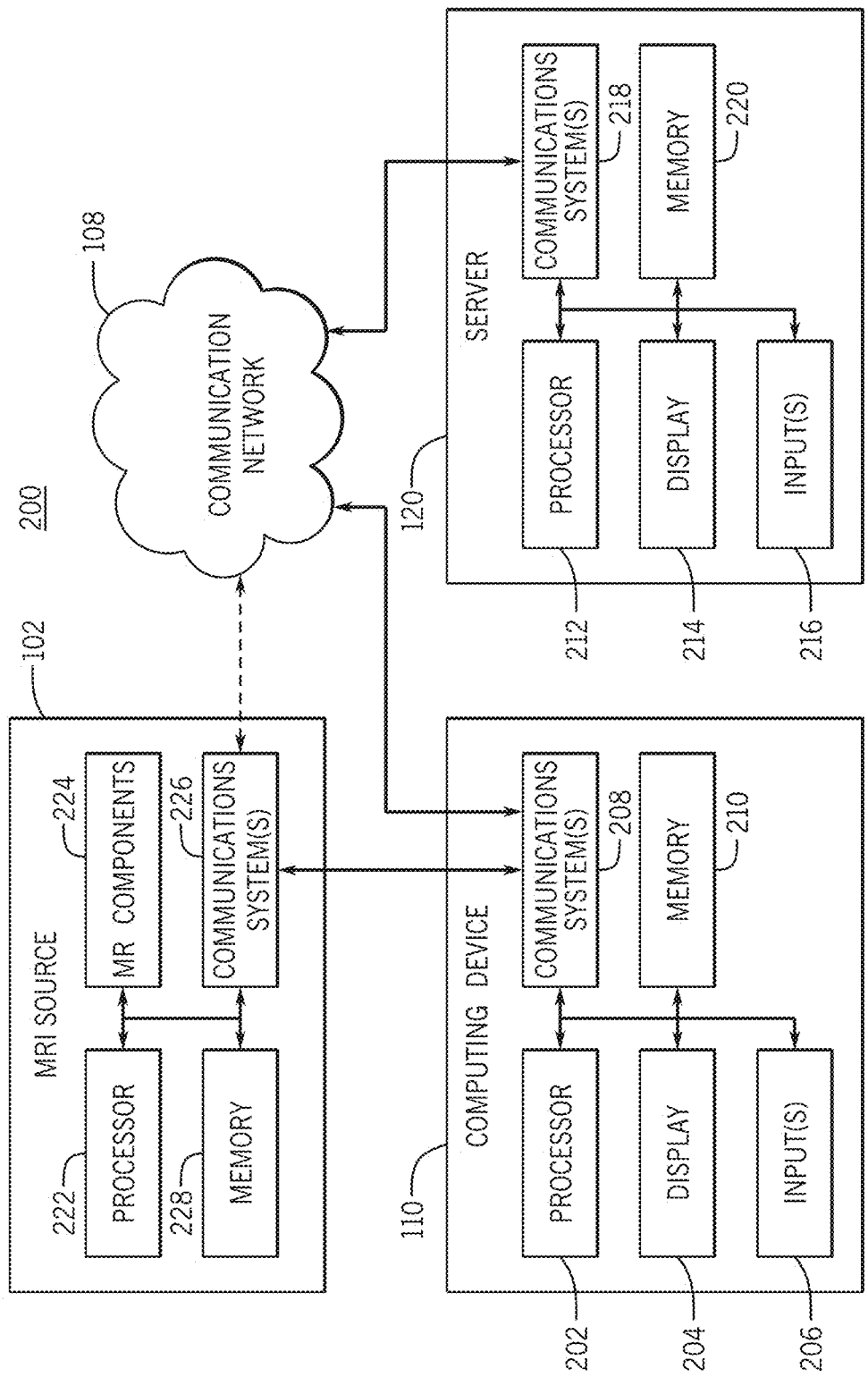
FIG. 2 shows an example of hardware that can be used to implement an MRI source, a computing device, and/or a server in accordance with some embodiments of the disclosed subject matter.

FIG. 2 shows an example 200 of hardware that can be used to implement MRI source 102, computing device 110, and/or server 120 in accordance with some embodiments of the disclosed subject matter. As shown in FIG. 2, in some embodiments, computing device 110 can include a processor 202, a display 204, one or more inputs 206, one or more communication systems 208, and/or memory 210. In some embodiments, processor 202 can be any suitable hardware processor or combination of processors, such as a central processing unit (CPU), a graphics processing unit (GPU), etc. In some embodiments, display 204 can include any suitable display devices, such as a computer monitor, a touchscreen, a television, etc. In some embodiments, inputs 206 can include any suitable input devices and/or sensors that can be used to receive user input, such as a keyboard, a mouse, a touchscreen, a microphone, etc.

In some embodiments, communications systems 208 can include any suitable hardware, firmware, and/or software for communicating information over communication network 108 and/or any other suitable communication networks. For example, communications systems 208 can include one or more transceivers, one or more communication chips and/or chip sets, etc. In a more particular example, communications systems 208 can include hardware, firmware and/or software that can be used to establish a Wi-Fi connection, a Bluetooth connection, a cellular connection, an Ethernet connection, etc.

In some embodiments, memory 210 can include any suitable storage device or devices that can be used to store instructions, values, etc., that can be used, for example, by processor 202 to present content using display 204, to communicate with server 120 via communications system(s) 208, etc. Memory 210 can include any suitable volatile memory, non-volatile memory, storage, or any suitable combination thereof. For example, memory 210 can include RAM, ROM, EEPROM, one or more flash drives, one or more hard disks, one or more solid state drives, one or more optical drives, etc. In some embodiments, memory 210 can have encoded thereon a computer program for controlling operation of computing device 110. In some embodiments, processor 202 can execute at least a portion of the computer program to present content (e.g., MRI data, results of automatic lesion diagnosis, user interfaces, graphics, tables, etc.), receive content from server 120, transmit information to server 120, etc.

In some embodiments, server 120 can include a processor 212, a display 214, one or more inputs 216, one or more communications systems 218, and/or memory 220. In some embodiments, processor 212 can be any suitable hardware processor or combination of processors, such as a CPU, a GPU, etc. In some embodiments, display 214 can include any suitable display devices, such as a computer monitor, a touchscreen, a television, etc. In some embodiments, inputs 216 can include any suitable input devices and/or sensors that can be used to receive user input, such as a keyboard, a mouse, a touchscreen, a microphone, etc.

In some embodiments, communications systems 218 can include any suitable hardware, firmware, and/or software for communicating information over communication network 108 and/or any other suitable communication networks. For example, communications systems 218 can include one or more transceivers, one or more communication chips and/or chip sets, etc. In a more particular example, communications systems 218 can include hardware, firmware and/or software that can be used to establish a Wi-Fi connection, a Bluetooth connection, a cellular connection, an Ethernet connection, etc.

In some embodiments, memory 220 can include any suitable storage device or devices that can be used to store instructions, values, etc., that can be used, for example, by processor 212 to present content using display 214, to communicate with one or more computing devices 110, etc. Memory 220 can include any suitable volatile memory, non-volatile memory, storage, or any suitable combination thereof. For example, memory 220 can include RAM, ROM, EEPROM, one or more flash drives, one or more hard disks, one or more solid state drives, one or more optical drives, etc. In some embodiments, memory 220 can have encoded thereon a server program for controlling operation of server 120. In some embodiments, processor 212 can execute at least a portion of the server program to transmit information and/or content (e.g., MRI data, results generated by automatic lesion diagnosis system 104, a user interface, etc.) to one or more computing devices 110, receive information and/or content from one or more computing devices 110, receive instructions from one or more devices (e.g., a personal computer, a laptop computer, a tablet computer, a smartphone, etc.), etc.

In some embodiments, MRI source 102 can include a processor 222, magnetic resonance (MR) components 224, one or more communications systems 226, and/or memory 228. In some embodiments, processor 222 can be any suitable hardware processor or combination of processors, such as a CPU, a GPU, etc. In some embodiments, MR components 224 can be any suitable components to generate MRI data corresponding to one or more MRI imaging modes (e.g., T1 imaging, T2 imaging, Diffusion Weighted Imaging, fMRI, etc.). An example of an MRI machine that can be used to implement MRI source 102 can include a conventional MRI scanner (e.g., a 1.5 T scanner, a 3 T scanner), a high field MRI scanner (e.g., a 7 T scanner), an open bore MRI scanner, etc.

Note that, although not shown, MRI source 102 can include any suitable inputs and/or outputs. For example, MRI source 102 can include input devices and/or sensors that can be used to receive user input, such as a keyboard, a mouse, a touchscreen, a microphone, a trackpad, a trackball, hardware buttons, software buttons, etc. As another example, MRI source 102 can include any suitable display devices, such as a computer monitor, a touchscreen, a television, etc., one or more speakers, etc.

In some embodiments, communications systems 226 can include any suitable hardware, firmware, and/or software for communicating information to computing device 110 (and, in some embodiments, over communication network 108 and/or any other suitable communication networks). For example, communications systems 226 can include one or more transceivers, one or more communication chips and/or chip sets, etc. In a more particular example, communications systems 226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 228 can include any suitable storage device or devices that can be used to store instructions, values, MRI data, etc., that can be used, for example, by processor 222 to: control MRI components 224, and/or receive MR data from MR components 224; generate MRI data; present content (e.g., MRI images, a user interface, etc.) using a display; communicate with one or more computing devices 110; etc. Memory 228 can include any suitable volatile memory, non-volatile memory, storage, or any suitable combination thereof. For example, memory 228 can include RAM, ROM, EEPROM, one or more flash drives, one or more hard disks, one or more solid state drives, one or more optical drives, etc. In some embodiments, memory 228 can have encoded thereon a program for controlling operation of MRI source 102. In such embodiments, processor 222 can execute at least a portion of the program to generate mp-MRI data, such as T2w MRI data, ADC MRI data, transmit information and/or content (e.g., MRI data) to one or more computing devices 110, receive information and/or content from one or more computing devices 110, receive instructions from one or more devices (e.g., a personal computer, a laptop computer, a tablet computer, a smartphone, etc.), etc.

Figure 3:
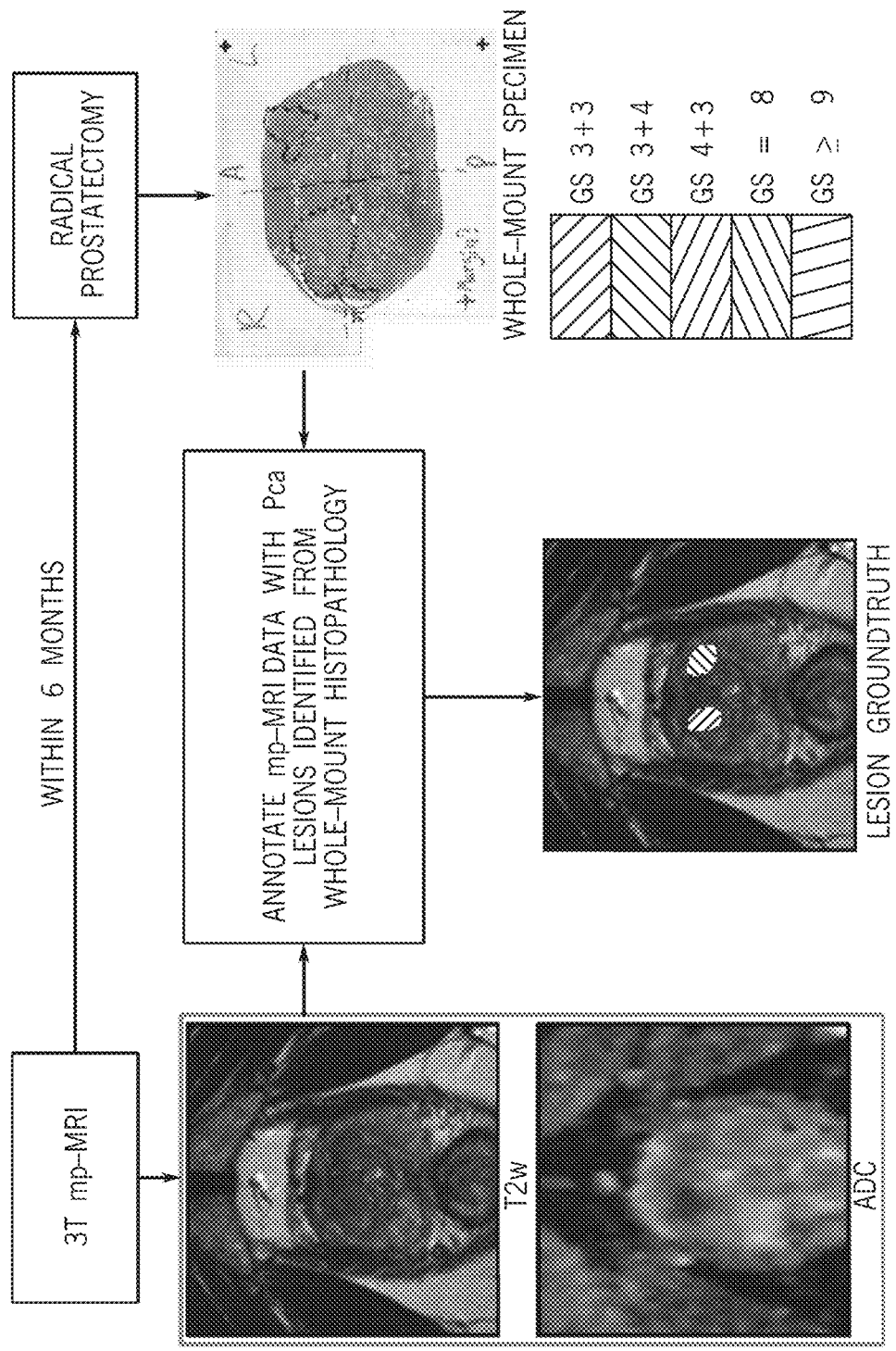
FIG. 3 shows an example of a procedure that can be used to label mp-MRI data in accordance with some embodiments of the disclosed subject matter.

FIG. 3 shows an example of a procedure that can be used to label mp-MRI data in accordance with some embodiments of the disclosed subject matter. As shown in FIG. 3, whole-mount histopathology specimens can be prepared from a patient's prostate after a radical prostatectomy (e.g., via a RALP procedure), and an expert can annotate the whole-mount histopathology specimens to indicate portions of the specimens that correspond to lesions, and GS level associated with each of the lesions. The annotated whole-mount histopathology specimens can be used to label mp-MRI data that was generated prior to the radical prostatectomy that depicts the patient's prostate in vivo. For example, the mp-MRI data can be data from a pre-operative scan that was taken within a particular period of time prior to the radical prostatectomy, such as within 6 months, 3 months, etc. In some embodiments, the period of time can be within the average amount of time that passes between a prostate cancer diagnosis and a radical prostatectomy. The labeled mp-MRI data can then be used to train a machine learning model (e.g., a CNN) to automatically segment and diagnose prostate lesions in novel mp-MRI data depicting a prostate.

In a particular example, labeled mp-MRI data that was used to train and validate a machine learning model that was used to implement an example system for automatically segmenting and diagnosing prostate lesions in accordance with some embodiments of the disclosed subject matter was generated using the procedure described in connection with FIG. 3. Pre-operative mp-MRI exams from 417 subjects who later underwent RALP were used to generate groundtruth data for training a CNN. Such data can be used, for example to train a CNN as described below in connection with FIGS. 4, 6A, and 6B. Note that mp-MRI data from subjects with prior radiotherapy or hormonal therapy was not used.

All imaging was performed on one of four different 3 T scanners (126 patients on Trio, 255 patients on Skyra, 17 patients on Prisma, and 19 patients on Verio; Siemens Healthcare, Erlangen, Germany) with a standardized clinical mp-MRI protocol, including T2w and DWI. Note that DCE-MRI was excluded because of its limited role in the current diagnostic practice. However, DCE-MRI data can be used in addition to, or in lieu of, data from one or more other components (e.g., T2w or ADC). The T2w data was generated using axial T2w turbo spin-echo (TSE) imaging techniques. Maps of the apparent diffusion coefficient (ADC) were generated using echo-planar imaging (EPI) DWI sequence techniques. For T2w, the repetition time (TR) and echo time (TE) of the T2w TSE were 3800-5040 milliseconds (ms) and 101 ms, respectively. With a 14 centimeter (cm) field of view (FOV) and a matrix size of 256×205, T2w TSE images were acquired and reconstructed with 0.55 mm×0.68 mm in-plane resolution and 3 mm through-plane resolution with no gaps. For DWI, TR and TE of 4800 ms and 80 ms were used. With a FOV of 21 cm×26 cm and matrix of 94×160, DWI images were reconstructed with in-plane resolution of 1.6 square millimeters ($mm^2$) and a slice thickness of 3.6 millimeters (mm). The ADC maps were obtained by using linear least squares curve fitting of pixels (in log scale) in the four diffusion-weighted images against their corresponding b values (0/100/400/800 s/$mm^2$).

The mp-MRI exams were reviewed by three GU radiologists (each having 10+ years of clinical prostate MRI reading) as part of the subject's standard clinical care. The findings with PI-RADS score ≥3 were reported and considered to be MRI-positive findings. The rest of the findings with PI-RADS ≤2 were considered to be MRI-negatives for the purposes of the study.

The whole-mount histopathology after RALP was prepared by slicing the excised prostate from apex to base with a 4-5 mm increment at the approximated mp-MRI orientation. Histopathology examinations of whole-mount specimens were performed by GU pathologists, blinded to all MRI information.

Later, at least one GU radiologist and one GU pathologist re-reviewed mp-MRI and histopathology examinations together at a multidisciplinary meeting. Each ROI in the mp-MRI data was matched to a corresponding location on the specimen through visual co-registration. MRI-positive findings were considered to be either true positive if they were in the same quadrant (e.g., left and right, anterior and posterior) and in the appropriate segment (e.g., base, midgland, and apex) on both mp-MRI and histopathology, or false positive if no corresponding lesions were found on the histopathology.

After the multidisciplinary meeting, GU radiology research fellows, supervised by GU radiologists, retrospectively reviewed each mp-MRI exam, referring to whole-mount histopathology, and annotated all MRI-visible lesions. 69.5% (278 out of 400) of prospectively missed (false negative) lesions were retrospectively identified in the review of the MRI and were annotated. The remaining 122 lesions that were identified via the whole-mount histopathology were considered MRI non-visible lesions and were not included in the groundtruth labeling due to the difficulty of the annotation.

Overall, 728 lesions were labeled in the mp-MRI data, which included 286 GS 3+3 lesions, 270 GS 3+4 lesions, 110 GS 4+3 lesions, 30 GS=8 lesions, and 32 GS>9 lesions. Among these, 93 GS 3+3 lesions, 204 GS 3+4 lesions, 98 GS 4+3 lesions, 26 GS=8 lesions, and 29 GS≥9 lesions were prospectively identified by radiologists from the pre-operative mp-MRI data. All annotations were made on the T2w data. An index lesion was defined for each patient as the lesion with the highest GS or the largest diameter when multiple lesions had the same grade on the histopathology, and clinically significant lesions were defined as lesions with GS≥7.

Figure 4:
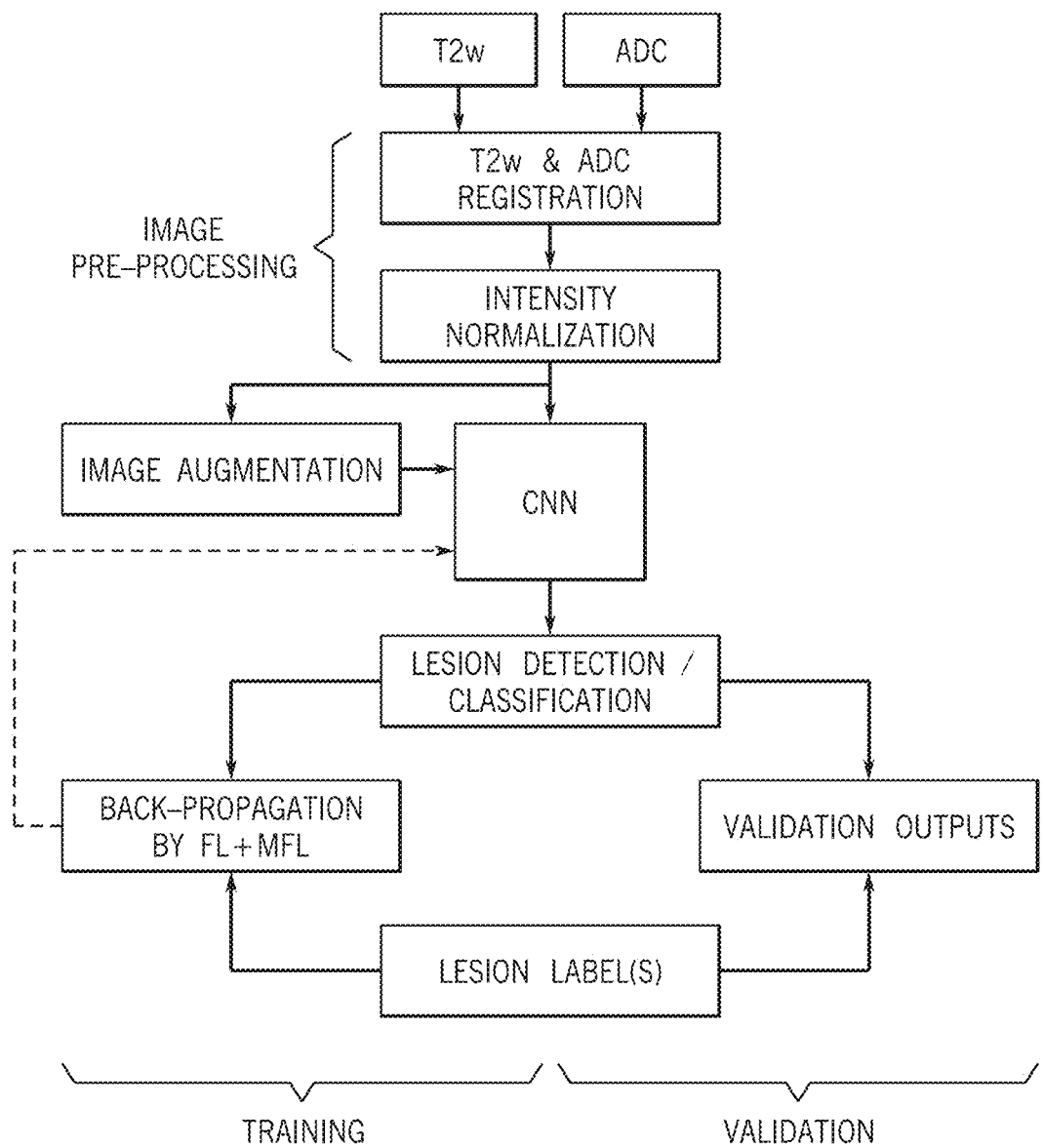
FIG. 4 shows an example of a flow that can be used for training mechanisms for automatically diagnosing prostate lesions using mp-MRI data in accordance with some embodiments of the disclosed subject matter.

FIG. 4 shows an example of a flow that can be used for training mechanisms for automatically diagnosing prostate lesions using mp-MRI data in accordance with some embodiments of the disclosed subject matter. In some embodiments, mechanisms described herein can be implemented using an end-to-end multi-class CNN that is configured to jointly detect PCa lesions and predict a GS for the detected lesions. As shown in FIG. 4, the mechanisms described herein can provide corresponding components of mp-MRI data, shown in FIG. 4 as T2w and ADC slices into two imaging channels as input to the CNN, which can predict pixel-level labels for each of six classes: non-lesion, GS 3+3, GS 3+4, GS 4+3, GS=8, and GS≥9.

Note that, in general, there can be large intensity variations between mp-MRI exams that are taken with and without the usage of an endorectal coil, and, as a result, commonly used normalization techniques using histogram data do not produce consistent results. In some embodiments, the mp-MRI data can be normalized using any suitable technique or combination of techniques for training and validation purposes and/or for input to the trained CNN. For example, the T2w data can be normalized by clipping the T2w intensity value using a lower threshold corresponding to the intensity of air and an upper threshold corresponding to the intensity of bladder. The bladder is relatively easy to locate programmatically, and the intensity of bladder is correlated with water and remains relatively consistent across subjects. After clipping, the T2w intensity can be linearly normalize to correspond to a range [0, 1] using the lower and upper thresholds. As another example, the ADC data can be normalized by clipping the ADC intensity based on subject-independent thresholds and then can be normalized to the range [0, 1], because ADC is a quantitative imaging modality and its intensity value is indicative of lesion detection and classification. During training, T2w intensity variations can be added to improve the robustness of the trained CNN to variable image intensity (e.g., caused by the presence or absence of the endorectal coil during scanning). For example, in some embodiments, the T2w upper-intensity threshold can be randomly fluctuated in the estimated range that PCa lesions are detectable after intensity normalization, which was determined empirically to from −15% to +20%.

In some embodiments, the ADC images can be registered to T2w images via rigid transformation using scanner coordinate information. Since ADC and T2w sequences are temporally close to each other in the scanning protocol that was used, minimal subject motion was present between the ADC and T2w data. Accordingly, additional non-rigid registration was not used. However, if the components of the mp-MRI that are used are less temporally close, additional non-rigid registration techniques can be applied to map the labeled lesions from the T2w data to another component. For the purposes of training, after the registration, an 80 mm×80 mm region centered on the prostate was identified manually for each subject, and was then converted to a 128×128 pixel image.

In some embodiments, image registration can be implemented using a statistical parametric mapping toolbox (e.g., as described in Friston et al., "Statistical Parametric Maps in Functional Imaging: A General Linear Approach," Human Brain Mapping, Vol. 2, no. 4, pp. 189-210 (1994), which is hereby incorporated by reference herein in its entirety). Note that the pre-processing techniques described above required roughly one minute for the images of each case without image processing optimizations.

FIG. 5 shows an example of a comparison of different techniques for encoding lesion classifications. Conventional multi-class CNNs typically encode each label into a one-hot vector (i.e., a vector of zeros with a single non-zero value, with the position of the non-zero value corresponding to the class represented in the sample being labeled) and the CNN predicts the one-hot vector corresponding to a particular diagnosis through the multi-channel output. As shown in FIG. 5, the six different labels described herein can be converted into 6-bit one-hot vectors. However, as described above, one-hot encoding assumes that different labels are unrelated to each other, and thus the cross-entropy loss penalizes misclassifications equally. Accordingly, the progressiveness between different GS, such that the treatment prognosis of a GS 4+4 PCa is more similar to GS 4+3 than to GS 3+3, is not accounted for in conventional one-hot encoding. Additionally, by dividing lesions into separate classes, the number of samples in each class is typically very limited.

As described herein, the labels from the six classes described herein can be converted into 5-bit ordinal vectors using ordinal encoding. As shown in FIG. 5, each bit of an ordinal vector identifies a non-mutually-exclusive condition, such that the k-th bit indicates whether the label is from a class greater or equal to k. Using such an encoding scheme, the groundtruth can be encoded into a 5-channel mask, e.g., the first channel is the mask for all lesions, the second channel is the mask for clinically significant lesions, etc. Then, the CNN can predict for the encoded mask using a 5-channel output, and a sigmoid function can be applied on top of each output channel to normalize the output into the prediction probability from zero to one (i.e., into a range [0,1]). For example, the first output channel can predict lesion detection probabilities.

Given a predicted ordinal encoded vector for a pixel, $\hat{y}=(\hat{y}_1,\hat{y}_2,\hat{y}_3,\hat{y}_4,\hat{y}_5)\in\{0,1\}$, the predicted class can be classified as the highest class k such that $\hat{y}_i=1 \forall i \leq k$, or non-lesion if $\hat{y}=0 \forall i$. The predicted class can be expressed alternatively as $$\max_{1\leq k\leq 5}\left(\prod_{i=1}^{k}\hat{y}_i\right)\left(\sum_{i=1}^{k}\hat{y}_i\right).$$

As described herein, ordinal encoding can be used to characterize relationships between different labels. For example, the ordinal vector corresponding to GS=8 shares 4 bits in common with the ordinal vector for GS 4+3, while sharing only 1 bit with the ordinal vector for non-lesion. These similarities and dissimilarities between labels can be represented as the shared and distinct bits in the ordinal vectors. As a result, ordinal encoding can allow a multi-class CNN to simultaneously learn features that are common across lesions of all different types, and features that are distinct between different GS. Additionally, although ordinal encoding does not increase the number of samples directly, by providing additional data points (e.g., through the use of the 5 channel masks) each channel has a larger joint population of lesions compared with one-hot encoding.

FIG. 6A shows a more particular example of a flow that can be used to train mechanisms for automatically diagnosing prostate lesions using mp-MRI data in accordance with some embodiments of the disclosed subject matter. As describe above in connection with FIG. 5, the lesion groundtruth can first be converted into a 5-channel groundtruth mask via ordinal encoding corresponding to five output channels of the CNN. The CNN can then generate a prediction, for each channel, corresponding to each channel of the groundtruth mask. In some embodiments, the CNN can be trained simultaneously using focal loss (FL) techniques with regard to both T2w and ADC and mutual finding loss (MFL) techniques for PCa features from one of the imaging components (e.g., the PCa features in the other component can be ignored if they are less useful for identifying the lesions in particular mp-MRI data).

In general, non-lesion labels and PCa lesion labels are very imbalanced at the pixel-level in the groundtruth data due to the relatively large ratio of normal tissue to PCA lesions. In the dataset used to implement a system for automatically diagnosing prostate lesions using mp-MRI data that was used to generate the results described herein (e.g., in connection with FIGS. 8-15), non-lesion pixels outnumbered lesion pixels by a ratio of about 62:1. After ordinal encoding for GS, the positive bit ratio of the groundtruth mask was only 0.77%. As a result, if lesion and non-lesion pixels were weighted equally, the cross-entropy loss can be overwhelmed by the amount of non-lesion terms, many of which correspond to easily predicted non-lesion pixels (i.e., pixels that the CNN predicts are non-lesion with a high probability of success). Lesion-related terms, on the other hand, would generally have little emphasis.

In some embodiments, to mitigate this imbalance, FL techniques can be used to balance learning between lesion and non-lesion pixels. FL can be used to add a focal weight of $(1-p_T)^2$ to the binary cross-entropy loss, where $p_T$ is the prediction probability for the true class. Using this technique, the impact of true predictions with high confidence on the total loss can be reduced. For example, in a common scenario during training a pixel that clearly corresponds to non-lesion tissue (e.g., a pixel with high ADC intensity, or a pixel located outside of prostate gland) may receive a 0.95 or greater prediction probability of being non-lesion, which would contribute 0.022 to conventional cross-entropy loss while only contributing $5.6\times10^{-5}$ to the FL. By down-weighting easily predicted pixels, the training can be focused on harder-to-predict (e.g., suspicious) pixels. FL can be further adapted to the ordinal encoding. For example, in some embodiments, if $\vec{y}=(y_1,y_2,y_3,y_4,y_5)\in\{0,1\}$ if the groundtruth encoded vector for a given pixel, corresponding to the 5-channel prediction probability vector $\vec{p} = (p_1, p_2, p_3, p_4, p_5) \in [0,1]$, then, the FL for each pixel can be represented using the following expression:

$$FL(\vec{p}) = q(\vec{p})\Sigma_{i=1}^{5} -\alpha y_i \log(p_i) - (1-\alpha)(1-y_i)\log(1-p_i), \quad (1)$$

where q is the focal weight defined as the largest margin between the prediction probability and the groundtruth among the five channels, with the weight defined according to the following expression:

$$q(\vec{p}) = \max_{1 \le j \le 5} y_j(1-p_j)^2 + (1-y_j)p_j^2. \quad (2)$$

Using these techniques, high-grade lesions can receive large focal weights if they are missed or downgraded by the CNN, which can result in the CNN being trained to give more weight to features predictive of high-grade lesions for lesion detection.

Additionally, in EQ. (1), $\alpha$ is a constant that controls the penalty between false negative and false positive predictions. In some embodiments, it may desirable to have a smaller penalty for false positives in PCa detection, since certain benign non-lesions, such as benign prostatic hyperplasia and benign adenomas, sometimes have a similar appearance to PCa lesions. Consequently, a large penalty for false positives may hinder the learning of true positive PCa features. Additionally, in some embodiments, a max spatial pooling filter can be applied to the focal weight q before the calculation of FL, which can maintain consistent weights for positive and negative pixels around lesion boundaries. In a particular example, $\alpha$ can be set to 0.75 for better sensitivity, while the max pooling filter can be sized to 3×3.

In conventional interpretation of prostate mp-MRI, a radiologic finding is initially identified from a single component (e.g., T2w data) and later consolidated or rejected after referencing to other imaging components (e.g., ADC data). The PI-RADS v2 score is then assessed primarily based on the finding's suspiciousness in the specific imaging component which describes the finding most clearly. Accordingly, many CAD systems have been developed to also mimic this procedure and determine PCa lesions from an individual imaging component as well as from the correspondence between multiple components of mp-MRI to comply with best practices that have been developed. However, the underlying challenge is that different components of mp-MRI capture distinct information, and not all of the information is shared across all components (e.g., certain features indicative of the presence of a lesion may be more prominent in one component than another for certain types of lesions, while the opposite may be true for another type of lesion). As a result, findings observable in one component may be only partially observable or not at all observable in the other component(s). Consequently, during end-to-end training using this conventional approach, a CNN with stacked imaging components may be able to effectively learn the common features across components, but there is no mechanism to train for features observable in only a specific imaging component(s).

In some embodiments, MFL techniques can be used to identify which imaging component contains distinct PCa features (and/or contains more distinct PCa features), and the identified component can be used to train for those distinct PCa features. For example, in some embodiments, given a training slice, MFL can be used to determine whether the T2w or ADC component alone can provide more information to allow the CNN to correctly classify lesions based on the classification of the groundtruth lesion(s). As shown in FIG. 6A, T2w and ADC can be individually passed into the same CNN with a blank image with all zeros to substitute for the other component (e.g., the different combinations can be provided as serial inputs to the CNN, not simultaneous parallel inputs to different channels of the CNN, with the combined information can first be input to the CNN and the CNN can provide corresponding outputs, then the T2w information with blank information on the ADC channel can be input to the CNN and the CNN can provide corresponding outputs based on only the T2w information, and so on). In such an example, the CNN prediction output from ADC alone (e.g., $f_{ADC} = f(I_{ADC}, I_{blank})$ and T2w alone (e.g., $f_{T2w} = f(I_{blank}, I_{T2w})$) can each be compared with the output using both components (e.g. $f_{out} = f(I_{ADC}, I_{T2w})$). The component resulting in a prediction output more similar to $f_{out}$ on the groundtruth lesion region can be considered to contain more PCa features, and can be selected as the component to use in training the CNN for this sample.

In some embodiments, having selected a component to use for training, MFL can train the CNN so that lesion findings can be equivalently observed from the selected imaging component alone. For example, MFL can minimize the L2-distance on the groundtruth mask y between $f_{out}$ and the output using the selected component, which can be expressed as $L2_{ADC} = \|y \otimes (f_{out} - f_{ADC})\|^2$ or $L2_{T2w} = \|y \otimes (f_{out} - f_{T2w})\|^2$, where $\otimes$ is the element-wise product. The L2-distance can be calculated on the groundtruth lesion region while not being calculated for the non-lesion regions, as MFL can be used to focus training on PCa features. Since non-lesion regions are more likely to have an appearance similar to lesions from the observation of a single component than from both components, enforcing $f_{ADC}$ or $f_{T2w}$ to have the same non-lesion finding of $f_{out}$ may counteract the training for PCa features. Moreover, $f_{out}$ can be utilized as a "soft" and adaptive truth reference to train for the specific component, compared with the groundtruth y. For example, when the CNN cannot detect a barely-visible lesion even with both components, $f_{out}$ would result in a low expectation that the CNN would be capable of identifying the lesion using a single imaging component. Conversely, the CNN can be trained for the certain PCa features in a single component if a lesion is clearly detected using both components, regardless of which component is selected.

As shown in FIG. 6A, the process of MFL can be summarized into a loss term for the end-to-end learning, which can be represented using the expression:

$$MFL = \frac{1}{N} \min\{L2_{ADC}, L2_{T2w}\}, \quad (3)$$

where N is the total number of pixels of an image. Note that while this describes MFL for two specific components of mp-MRI data, this is merely an example and MFL can be extended to additional components, which can be represented using the expression:

$$MFL = \min_{1 \le i \le m} \|y \otimes (f_{out} - f_i)\|^2, \quad (4)$$

In some embodiments, a CNN implemented using mechanisms described herein in accordance with some embodiments of disclosed subject matter can be trained using a combined loss from FL and MFL, which can be represented using the expression:

$$L = \mathbb{E}_{\vec{p} \sim S(f_{out})} FL(\vec{p}) + \lambda MFL, \qquad (5)$$

where S is the sigmoid function and λ=1/positive bit ratio is a constant weight to balance between FL and MFL. Note that, as shown in FIG. 6A, the arrows with outlined arrowheads indicate the back-propagation paths of FL, and the dashed arrows indicate back-propagation paths of MFL. Accordingly, as shown in FIG. 6A, the MFL can be inhibited from passing the gradient to $f_{out}$ to train with respect to both imaging components, since $f_{out}$ serves as a truth reference for $f_{ADC}$ or $f_{T2w}$ in MFL.

In some embodiments, the CNN depicted in FIG. 6A can be implemented using any suitable CNN topology. For example, the CNN depicted in FIG. 6A can be implemented using a Deeplab CNN with a 101-layer deep residual network on 2D image inputs and using ordinal vector encoding, which is sometimes referred to herein as "FocalNet." Examples of techniques that can be used to implement such a CNN are described in Chen et al., "Deeplab: Semantic image segmentation with deep convolutional nets, atrous convolution, and fully connected crfs," IEEE Transactions on Pattern Analysis and Machine Intelligence, Vol. 40, no. 4, pp. 834-848 (2018), and He et al., "Deep Residual Learning for Image Recognition," Proceedings of IEEE Conference on Computer Vision Pattern Recognition, pp. 770-778 (2016), each of which is hereby incorporated by reference herein in its entirety. As another example, the CNN depicted in FIG. 6A can be implemented using a U-Net CNN. However, training with U-Net often failed in early stages due to the model diverging, which may have been caused by incompatibility between FL and U-Net skip connections.

In some embodiments, the CNN can be initialized using weights generated based on a general object classification task (e.g., as described in Hoo-Chang et al., Deep convolutional neural networks for computer-aided detection: CNN architectures, dataset characteristics, and transfer learning," IEEE Transactions on Medical Imaging, Vol. 35, no. 5, p. 1285 (2016), which is hereby incorporated by reference herein in its entirety), which is sometimes referred to as transfer learning. In some embodiments, transfer learning techniques can further train the parameters of the hidden layers of a CNN, while in other transfer learning techniques, the parameters of the hidden layers can be kept constant, and only the output layers can be retrained to perform a different classification task. In the example of FIG. 6A, the weights of the hidden layers were further trained using a combination of FL and MFL techniques. Additionally, in some embodiments, output layers that replace the output layers of the CNN that was trained to perform that the general object classification task can be randomly initialized.

In some embodiments, the total loss can be optimized using any suitable technique or combination of techniques. For example, the total loss can be optimized using stochastic gradient descent with momentum 0.9 and L2-regularizer of weight 0.0001, with a learning rate that starts at 0.001 with 0.7 decay every 2000 steps. In such an example, the CNN can be trained for 200 epochs with batch size 16. Additionally, in some embodiments, T2w intensity variation and image augmentations (e.g., image shifting, image scaling, and image flipping) can also be applied during training. Note that the training examples used to generate the data described herein became blurry during interpolation when image rotations were applied, and hence image rotation was omitted. However, this is merely an example, and other data may not be similarly affected. In some embodiments, the image augmentations can be performed for each batch of the training images, but can be omitted for the validation images.

Figure 6B:
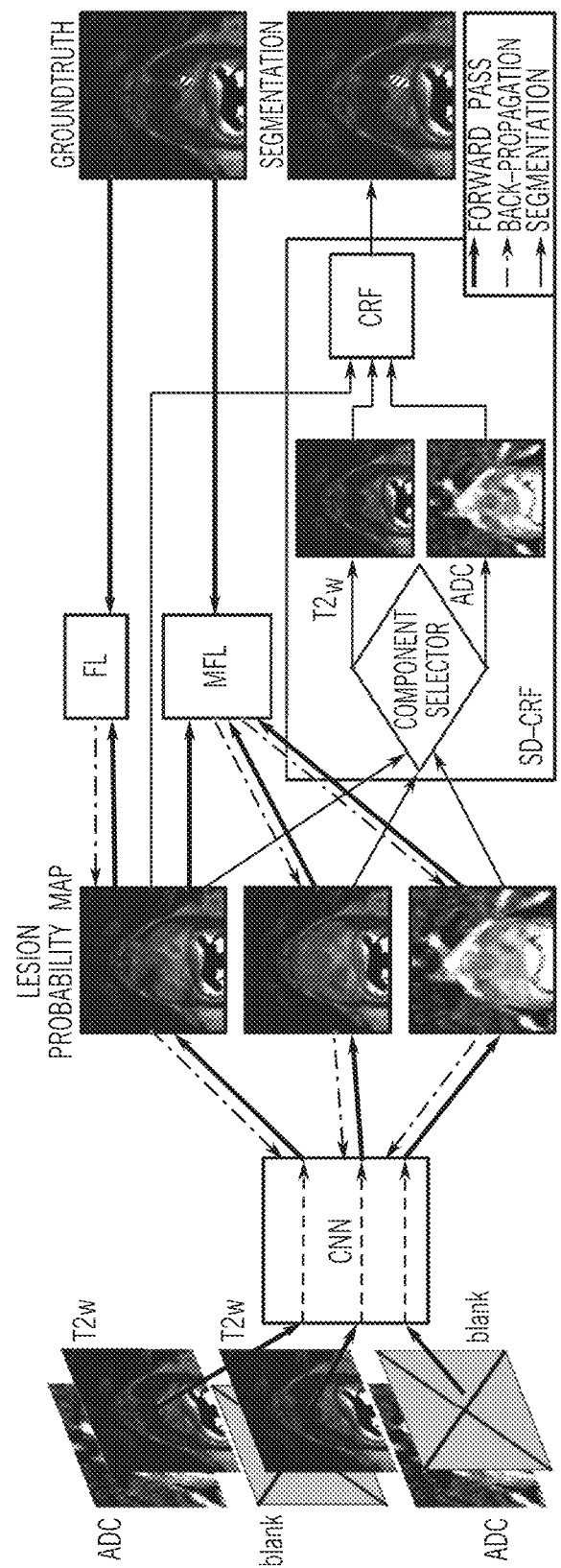
FIG. 6B shows another more particular example of a flow that can be used to train mechanisms for automatically diagnosing prostate lesions using mp-MRI data in accordance with some embodiments of the disclosed subject matter.

FIG. 6B shows another more particular example of a flow that can be used to train mechanisms for automatically diagnosing prostate lesions using mp-MRI data in accordance with some embodiments of the disclosed subject matter. As shown in FIG. 6B, in some embodiments, conditional random field techniques can be used to implement segmentation of lesions from the mp-MRI data. For example, selective dense conditional random field (SD-CRF) is a nonparametric post-processing step that can be used to fit a CNN probability map into the intensity pattern of a specific imaging component for the lesion segmentation that can indicate the probability of a lesion of any aggressiveness being present at a particular pixel (e.g., in addition to, or in lieu of, segmenting a lesion of a particular aggressiveness). SD-CRF can first determine whether ADC or T2w defines the lesion better using the component selector shown in FIG. 6B. In some embodiments, the component selector can compare the L2-distance on cancerous areas with either of the imaging components, and can select the component resulting in a smaller L2-distance. For example, the determination of which component to segment can be expressed as $$I_{Sel} = \arg\min_{c \in \{I_{ADC}, I_{T2w}\}} d(\hat{y} \otimes f_{out}, \hat{y} \otimes f_c),$$

where $f_{out}$ and $f_c$ are CNN outputs from both components combined ($f_{out}$) and from the specific imaging component c (i.e., in the example of FIG. 6B, either $f_{ADC}$ or $f_{T2w}$), and $\hat{y}=[f(I_{ADC}, I_{T2w})>0.5]$ approximates for the groundtruth y, as the groundtruth will be unavailable when attempting to segment novel mp-MRI data.

Figure 8:
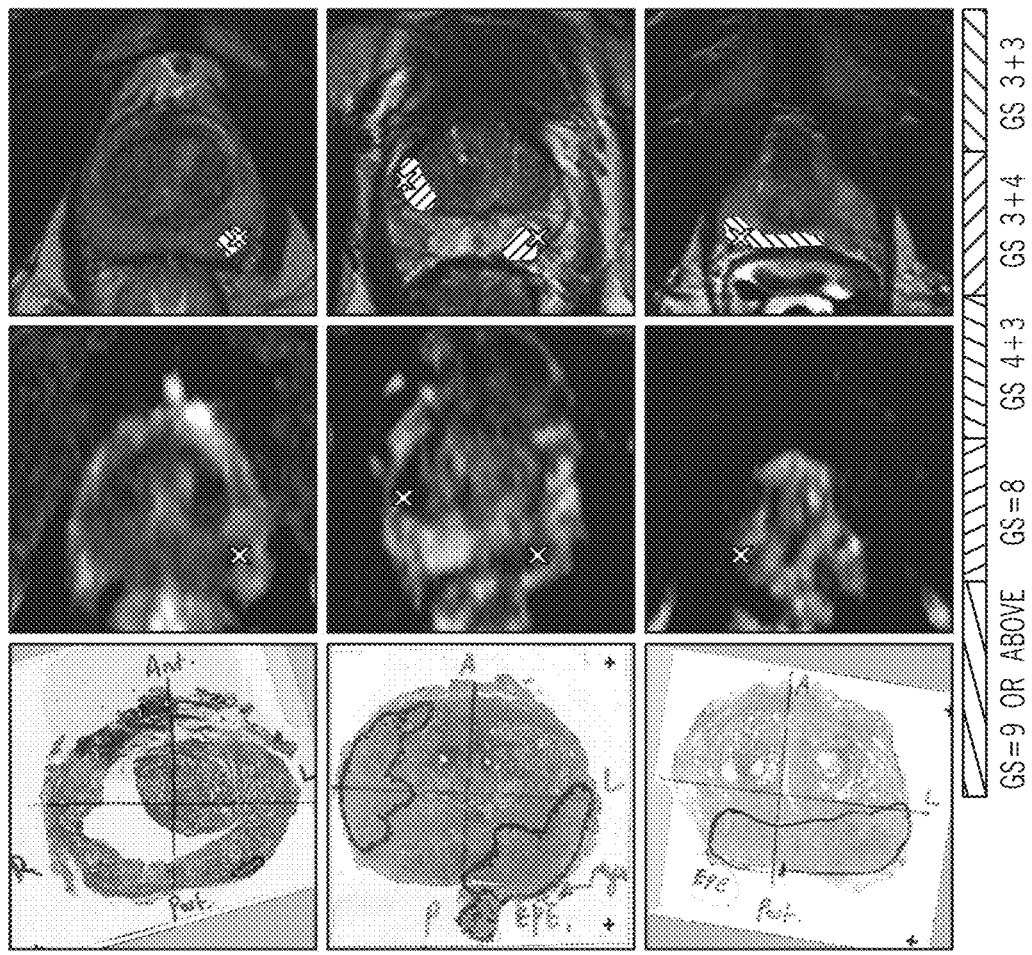
FIG. 8 shows an example of mp-MRI data labeled using mechanisms described herein, and a comparison to overlaid manually labeled contours and labeled whole-mount specimens of the prostates represented in the images.

In the example shown in FIG. 6B, a conditional random field can be built for a refined lesion segmentation mask y* with regard to the intensity pattern in the selected imaging component and the CNN output. Specifically, y* can be inferred by minimizing the energy E using the expression $$E(y^*) = \Sigma_{i=1}^N \phi_u(y^*_i | I_{ADC}, I_{T2w}) + \Sigma_{i<j}^N \phi_p(y^*_i, y^*_j | I_{Sel}), \qquad (6)$$

where $\phi_u$ is the unary potential from the negative log-likelihood of the CNN predicted probability map, and $\phi_p$ is the pairwise potential from ith and jth pixels, and N is the total number of pixels in the image component. In particular, the pairwise potential can be defined as $\phi_p(y^*_i, y^*_j | I_{Sel}) = -\exp(-d_{i,j}^2 - \Delta_{i,j}^2)$, where $d_{i,j}$ is the spatial distance between the ith and jth pixels in the selected component (e.g., the T2w image, or the ADC image), and $\Delta_{i,j}$ is the intensity difference between the ith and jth pixels in the selected component (e.g., the T2w image, or the ADC image). The unary potential $\phi_u$ can be inversely related to the likelihood that a particular pixel represents a lesion (e.g., based on a probability map based on an output by the CNN when both components were provided as input), such that pixels that are lower probability to be lesion are much less likely to be included in the mask y*, due to $\phi_u$ having a larger value for lower probability pixels. The pairwise potential $\phi_p$ can represent similarity between two pixels, such that as differences in intensity and/or physical distance between a pair of images in the selected image component increases, the pair of pixels is less likely to be included in the mask y*. Holding all else equal, as either the value of $d_{i,j}^2$ or $\Delta_{i,j}^2$ increases representing a larger divergence between the two pixels, the magnitude of the value of $\phi_p$ tends to decrease. Due to the pairwise potential $\phi_u$ having a weight of −1, the inclusion of pairs of pixels that are similar to one another produces large negative values of $\phi_u$ resulting in lower overall energy after the pairwise values are all subtracted from the sum of the unary potentials $\phi_u$. In some embodiments, segmentation mask y* can be optimized via an iterative approach, such as the approach described in Krahenbuhl et al., "Efficient inference in fully connected CRFs with Gaussian edge potentials," Advances in neural information processing, pp. 109-117 (2011), which is hereby incorporated by reference herein in its entirety. In some embodiments, the segmentation mask y* can be used to visualize the segmentation using various techniques, such as by at least partially occluding portions of the image component (e.g., T2w, ADC) that correspond to pixels identified as lesion by the segmentation mask. For example, each pixel for which the segmentation mask y* indicates lesion can be rendered in a particular color, and/or a partially transparent color can be added to the underlying image content such that an opaque or partially transparent object representing to the segmentation is rendered in association with an imaging component (e.g., as shown in FIGS. 6A, 6B, and 8). As another example, the segmentation mask y* can be used to draw an outline of one or more lesions by identifying pixels for which the segmentation mask y* indicates lesion, and which have at least one neighbor that is indicated as being non-lesion (i.e., pixels for which all neighbors are lesion can be ignored to avoid occluding the MR data corresponding to the lesion). In such an example, the identified pixels from the segmentation mask y* can be rendered in a particular color (e.g., partially transparent in combination with the underlying MR data, or in lieu of the MR data) or pattern to create an outline corresponding to an edge of the area identified as lesion by the segmentation mask y*. Alternatively, the neighboring pixel(s) the identified pixels from the segmentation mask y* can be rendered in a particular color (e.g., partially transparent in combination with the underlying MR data, or in lieu of the MR data) or pattern to create an outline that surrounds the area identified as lesion by the segmentation mask y*. Note that while the segmentation mask was described as being generated using data from a particular component, the mask can be used to visualize the lesion segmentation in any component of the mp-MRI data, since the data from different components can be co-registered.

Figure 7:
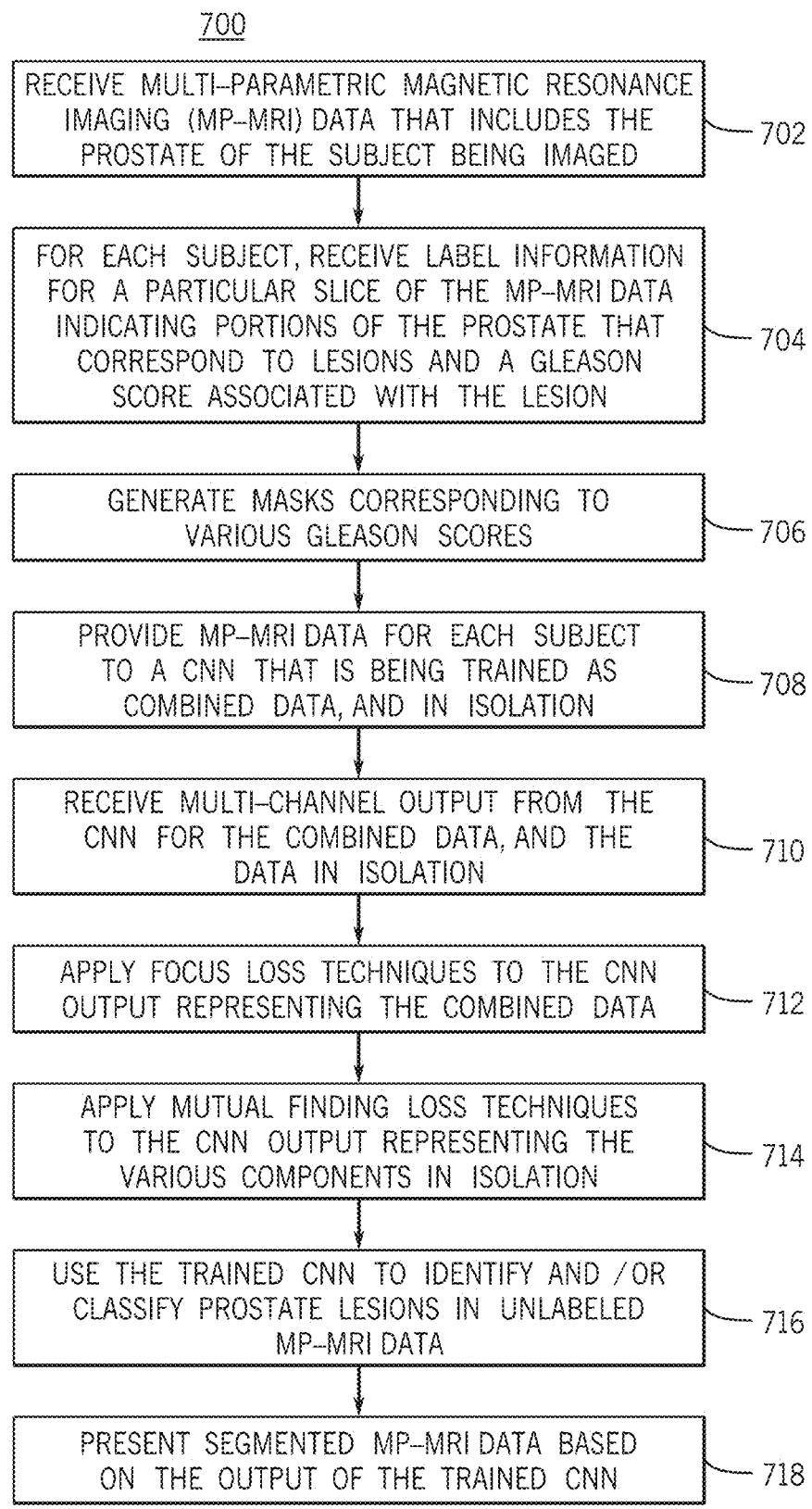
FIG. 7 shows an example of a process for training and using a system for automatically diagnosing prostate lesions using mp-MRI data in accordance with some embodiments of the disclosed subject matter.

FIG. 7 shows an example 700 of a process for training and using a system for automatically diagnosing prostate lesions using mp-MRI data in accordance with some embodiments of the disclosed subject matter. As shown in FIG. 7, at 702, process 700 can receive mp-MRI data that includes the prostate of various subjects. For example, MRI data corresponding to various subjects can be transmitted to and/or saved by a computing device that is to be used to train a CNN to be used in a system for automatically diagnosing prostate lesions using mp-MRI data. In some embodiments, as described above in connection with FIG. 3, the MRI data can correspond to subjects that later had a procedure to remove their prostate.

At 704, process 700 can receive label information for each subject for slices of the MRI data that include lesions indicating which portion of the data corresponds to a lesion (s), and a class associated with the lesion. For example, the MRI data can be labeled by segmenting a portion of the MRI data as corresponding to a lesion, and associating a GS with the lesion indicating the predicted aggressiveness of the lesion as classified by one or more experts based on an analysis of a tissue sample removed from the patient (e.g., based on a whole-mount histopathology specimen). For example, as described above in connection with FIG. 3, a user can indicate which portion(s) of a slice of MRI data corresponds to a lesion based on a visual co-registration with reference to a whole-mount histopathology of the prostate depicted in the image.

At 706, process 700 can generate masks corresponding to the class of lesion(s) depicted in a particular slice of MRI data. For example, as described above in connection with FIG. 6A, a mask can be generated for each category of GS corresponding to 1 bit of an ordinal vector used to represent the aggressiveness of a lesion with each mask indicating whether a lesion of at least the severity encoded by the mask is present at a particular pixel location. For example, if a pixel depicts non-lesion (e.g., normal prostate, non-prostate, etc.), each mask can be encoded with a zero for that pixel. As another example, if a pixel depicts a lesion classified as GS 4+3, the mask corresponding to GS 3+3 can be encoded with a 1 for that pixel, the mask corresponding to GS 3+4 can be encoded with a 1 for that pixel, and the mask for GS 4+3 can be encoded with a 1 for that pixel, while the masks for GS 8 and GS≥9 can be encoded with zeros, indicating that the lesion was annotated as being less severe than GS 8. In some embodiments, each mask can be a binary mask encoding whether each pixel is at least the GS severity encoded by that mask.

At 708, process 700 can provide mp-MRI data for each subject to a CNN as part of a training process both as combined data (e.g., providing T2w data to a first channel, and ADC data to a second channel), and in isolation (e.g., providing T2w data to the first channel, and blank information to the second channel, and providing blank information to the first channel and ADC data to the second channel). As described above, in some embodiments, the combined data and the isolated data can be provided to the CNN serially. For example, each permutation can be provided as input to the CNN, and the output from each input can be generated and used to generate an FL or MFL value. Note that while two components are generally described herein, this is merely an example, and more components can be incorporated into training by increasing the number of channels of the CNN (e.g., so that there is one channel for each component) and providing additional permutations to the CNN. For example, each individual component can be provided with blank version of the other components. As another example, different combinations of components can be provided, with one or more other components withheld (e.g., two components can be provided to the CNN, while a third channel is provided with blank data).

In some embodiments, the mp-MRI components used in training and/or validation can be pre-processed. For example, as described above in connection with FIG. 3, T2w data can be clipped based on subject-specific thresholds and normalized, while ADC data can be clipped and normalized using a non-subject-specific threshold.

At 710, process 700 can receive multi-channel output from the CNN being trained for the combined data, and different multi-channel output from the CNN being trained for each component in isolation. For example, as described above in connection with FIG. 6A, the CNN can output five values for each pixel corresponding to the five classes of GS encoded in the ordinal encoding scheme for each different set of input data. In such an example, because three different sets of inputs are provided to the CNN, this generates 15 values for each pixel (e.g., three vectors each having five elements).

At 712, process 700 can apply FL techniques to the CNN output representing the combined data to mitigate the bias produced by the relative abundance of normal tissue. For example, process 700 can apply FL techniques to the $f_{out}$ data to minimize the contribution of normal tissue pixels that were estimated at high probability, as described above in connection with FIG. 6A.

At 714, process 700 can apply MFL techniques to the CNN output representing the isolated data to favor the component of the mp-MRI data that provides more information that can be used to classify lesions in the mp-MRI data. For example, process 700 can apply MFL techniques to select whether to train the CNN based on the T2w data or the ADC data, depending on which is closer to the combined output $f_{out}$ to leverage the component that has features that better represent the lesion as described above in connection with FIG. 6A. As described above in connection with EQ. (5), a total loss value can be used during training that is based on a combination of the FL and MFL values calculated by comparing the CNN output to the ground truth ordinal masks.

At 716, after training is completed, process 700 can use the trained CNN to identify and/or classify prostate lesions in unlabeled mp-MRI data, which can be used to augment and/or supplement identification and classification by a medical practitioner.

In some embodiments, after training is complete, mp-MRI data can be provided to the trained CNN, which can provide output identifying a position and class of any lesions identified in the mp-MRI data. For example, process 700 can receive mp-MRI data corresponding to a patient's prostate (e.g., from MRI source 102), and can an 80 mm×80 mm region centered on the prostate can be identified, and then converted to a 128×128 pixel image. Any suitable technique can be used to identify the 80 mm×80 mm region to convert to the data to be input to the CNN. For example, user input can be received to place a user interface element of that size over the prostate in the T2w image, or by prompting a user to provide input indicating a center point of the prostate. As another example, process 700 can attempt to automatically identify the location of the prostate, and can present a user interface indicating the region that process 700 has indicated likely corresponds to the prostate, which can be adjusted by a user. In some embodiments, after identifying suitable prostate data, process 700 can pre-process the data to generate a suitable input for the CNN. For example, in some embodiments, as described above in connection with FIG. 3, process 700 can clipped the T2w data based on subject-specific thresholds and normalized, and clip the ADC data can be clipped and normalized using a non-subject-specific threshold. Process 700 can then provide the pre-processed T2w and ADC data to the CNN, and can receive outputs indicating the likelihood that each pixel of the input data is a particular GS, which can be used to generate an automatic segmentation of the prostate in the T2w data and/or one or more other components of the mp-MRI data (e.g., as described above in connection with FIG. 6B).

At 718, process 700 can cause an automatically segmented image to be presented indicating the location of one or more lesions identified by the trained CNN and the likely GS of the lesions(s). For example, an image similar to the images shown in the top panels of FIG. 8, or shown in the Segmentation of FIG. 6B and/or the Lesion probability maps of FIG. 6B can be presented to a user based on the output of the trained CNN. The presented segmented images can be used by the user to inform a diagnosis, and/or to help make decisions about whether further tests are likely to be useful.

In some embodiments, the segmentation can be presented to indicate the presence of a clinically significant lesion and a location at which the lesion is likely to be located. In some embodiments, information about a predicted GS classification that is generated by the CNN can be omitted from presentation with the segmentation information. For example, the segmentation can be presented with similar visual characteristics (e.g., using the same color) regardless of the underlying likelihood that the lesion corresponds to a particular GS level. In such an example, the segmentation can indicate the extent of a predicted clinically significant PCa lesion (e.g., a lesion having a GS>6). Alternatively, in some embodiments, information about the predicted likelihood of classification in a particular GS level can be presented in connection with the segmentation and/or separately from the segmentation. For example, in some embodiments, the segmentation can be visualized in connection with a probability map based on the output from a particular output channel of the CNN. As another example, the segmentation can be presented in a color or pattern that represents a most likely GS of a lesion that has been segmented based on the classification of each pixel of the combined data (e.g., based on $f_{out}$) corresponding to a particular segment. In a more particular example, a threshold can be used to determine whether each pixel corresponding to a particular lesion has been classified as belonging to a particular GS level, and the collective likelihood that the lesion belongs to a particular GS level can be determined based on whether a particular portion (e.g., ½, ⅔, etc.) of the pixels are classified at that GS level. As still another example, classification information can be presented in a report indicating a portion of pixels that were classified at each GS level, which can be indicative of the presence of a PCa lesion of that GS level in the mp-MRI data, and can inform a decision making process of a user (e.g., a radiologist, a urologist, an oncologist) in determining a course of treatment. In some embodiments, information presented at 718 can be provided to allow a user to make a more informed decision about whether to perform a biopsy, where to perform the biopsy, the urgency of performing a biopsy, etc.

FIG. 8 shows an example of mp-MRI data labeled using mechanisms described herein, and a comparison to overlaid manually labeled contours and labeled whole-mount specimens of the prostates represented in the images. As shown in FIG. 8, the top row represents labeled T2w MRI data with regions corresponding to prostate lesions outlined in a color corresponding to the classification of the lesion (i.e., represented using a Gleason Score), the middle row represents corresponding ADC data, and the bottom row depicts whole-mount specimens corresponding to the portion of the prostate depicted in the MRI data in the top and middle rows with portions corresponding to lesions outlined. Positions of lesions predicted by a CNN trained in accordance with the mechanisms described herein are shown with an x. Note that segmentation can be shown in various styles. For example, as shown in FIG. 8, segmentations can be shown as a patch at least partially occluding the MRI data that was segmented (e.g., the T2w image component). As shown in FIG. 8, the segmentation can be presented using a color or other differentiating characteristics indicating a GS associated with a lesion that has been segmented. Although the segmentations and legend shown in FIG. 8 and elsewhere (e.g., in FIG. 6A) using cross-hatching, this is merely to insure that the segmentations can be identified as being associated with a particular GS in the non-color submitted herewith and the different cross-hatchings can be replaced with different colors, for example as shown in Cao et al., "Joint Prostate Cancer Detection and Gleason Score Prediction in mp-MRI via FocalNet," IEEE Transactions on Medical Imaging, Vol. 38, Issue 11, pp. 2496-2506 (November 2019), which is hereby incorporated by reference herein in its entirety. However, this is merely an example, and the segmentation information can be presented using other styles. For example, an outline of the lesion can be presented with a color of the line corresponding to a predicted GS of the lesion.

Figure 9:
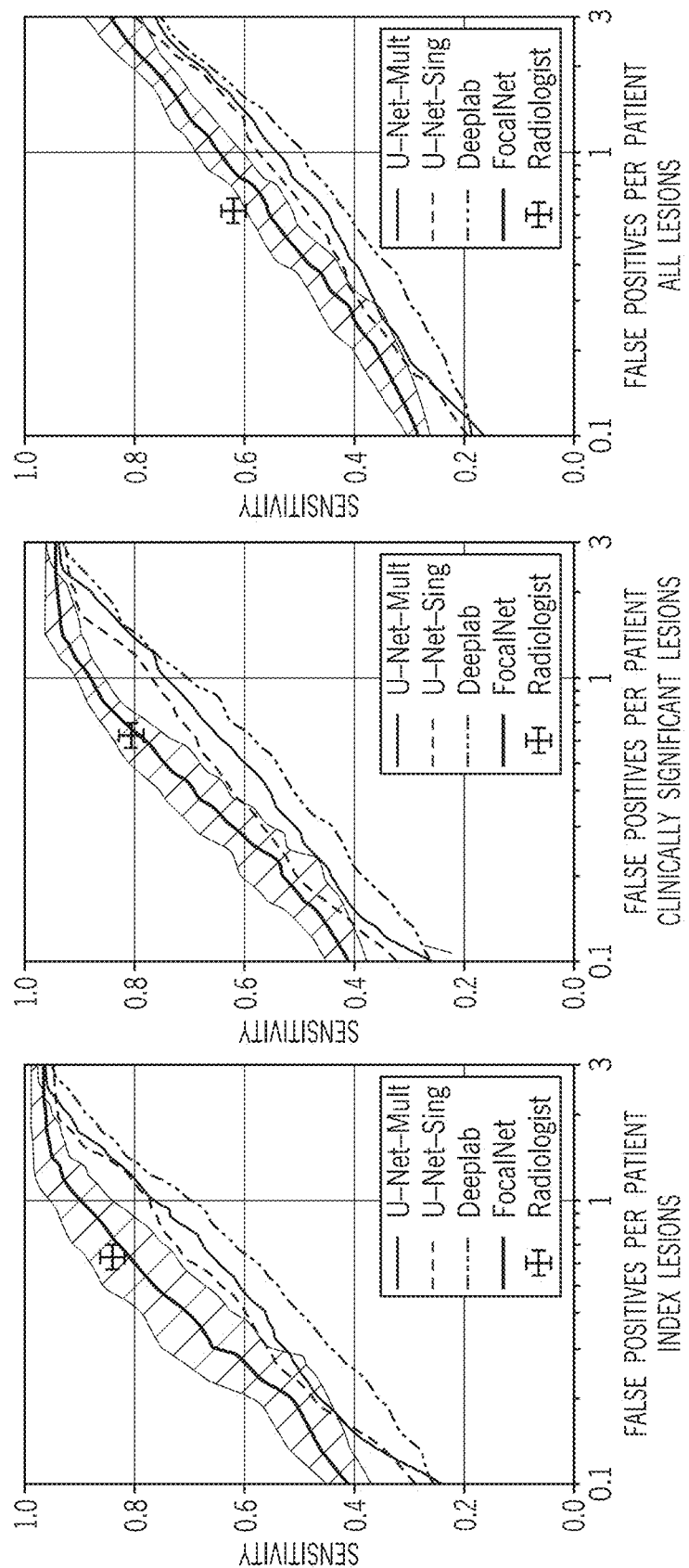
FIG. 9 shows example comparisons of sensitivity to prostate lesions achieved by various techniques including techniques based on the mechanisms described herein at various false positive rates.

FIG. 9 shows example comparisons of sensitivity to prostate lesions achieved by various techniques including techniques based on the mechanisms described herein at various false positive rates. Note that the results in the figures referred to as being associated with "FocalNet" were generated using a CNN implemented in accordance with some embodiments of the disclosed subject matter using both FL and MFL (e.g., as described above in connection with FIG. 6A) and using the training and validation data described in connection with FIG. 9. The TensorFlow machine learning framework (Google; Mountain View, Calif.) was used to implement mechanisms described herein, and the implementation was used to generate the classifications described below in connection with various results. The average training time was 3-4 hours for each fold using an NVIDIA Titan Xp GPU with 12 GB memory, and the prediction was relatively fast, at about 0.5-1 second for each subject, due to the non-iterative nature of CNNs.

The CNN was trained and validated using 5-fold cross-validation, with each fold including 333 or 334 training cases and 84 or 83 cases for validation. In both training and validation, only annotated slices were included in order to minimize the chance for miss-annotated lesions. Each case included from 2 to 7 slices, and each fold of training and validation sets included around 1400 and 350 slices, respectively.

For PCa detection, lesion localization points were extracted from CNN pixel-level detection output. For each case, 2D local maxima were found from the detection output of the slices. The trade-off between detection sensitivity and false detections can be controlled by thresholding on the detection probabilities of the local maxima.

The lesion detection performance was evaluated through free-response receiver operating characteristics (FROC) analysis to accommodate PCa's multi-focality. FROC measures the lesion detection sensitivity versus the number of false positives per patient. A detection was counted as a true positive detection when a localized point predicted by the CNN was in or within 5 mm of lesion ROIs since PCa lesion diameters on the whole-mount specimen are roughly 10 mm greater than the corresponding ROIs in mp-MRI. False positive detections were those localized points that are not true positive detections. Since the lesion groundtruth is annotated in 2D slices without the consideration of the 3D lesion volume, a localized point must be in the same slice of an ROI to be considered as a true detection. Lesion detection sensitivity is the number of detected lesions divided by the total number of visible lesions, including both the prospectively identified lesions and the prospectively missed lesions identified in the retrospective review described above in connection with FIG. 3. Because of the availability of whole-mount histopathology, the definition of true or false detection is likely more accurate than studies using only biopsy cores.

Additionally, the lesion detection performance is further described in fine-grained lesion groups as they have different detectabilities. For example, FROC for lesion detection of each specific GS group. Under this setting, lesion detection sensitivity considers only lesions in a specific GS group. Lesions with GS=8 and GS≥9 are grouped together since 1) either of them have very limited quantity in each fold of validation, and 2) difference in treatment indicated by either score is minimal.

The GS prediction was evaluated by receiver operative characteristic (ROC) analysis. The multi-class classification was grouped into four binary classification tasks: 1) GS≥7 vs. GS<7; 2) GS≥4+3 vs. GS≤3+4; 3) GS≥8 vs. GS<8; and 4) GS≥9 vs. GS<9. A voxel-level ROC was assessed for each task. Specifically, to mimic a biopsy setting, twelve detection voxels were sampled for each case by finding the localized points. In a joint model for detection and classification, this setting evaluates classification performance without being affected by lesion misdetection, since if a lesion is completely missed by the model, the classification result for the lesion is meaningless as well.

The results generated using an implementation of mechanisms described herein is compared with the prospective clinical performance of radiologists for lesion detection. Radiologist performance was assessed on the entire 417 cases grouped by the five validation sets. Radiologist's findings were determined to be true or false positives as described in connection with FIG. 3. The sensitivity is calculated on the number of true positive findings versus the total number of MRI-visible lesions.

Deeplab, U-Net-Mult, and U-Net-Sing are the three baseline techniques evaluated in the results depicted in FIGS. 9 to 11. Deeplab is the base model of the CNN depicted in FIG. 6A trained using cross-entropy loss and one-hot encoding (e.g., not using FL and MFL, and not using ordinal encoding). U-Net is a popular CNN architecture for various biomedical imaging segmentation tasks. U-Net-Mult (multi-class U-Net) was trained to detect and classify lesions using one-hot encoding while U-Net-Sing (single-class U-Net) was trained for a simplified task to detect lesions only, regardless of their GS. To enable a fair comparison, the same image pre-processing and image augmentation techniques were used during training and validation as described above in connection with FIG. 4 with all techniques, although the combination of FL and MFL during training, as well as the use of ordinal encoding masks were using only with the machine learning model implemented in accordance with mechanisms described herein (labeled "FocalNet" in FIGS. 9-13). Under the cross-validation setting, p-values were obtained by two-sample Welch's t-test, with the alpha level adjusted by Bonferroni correction for multiple comparisons.

Examples for lesion detection by the CNN implemented using mechanisms described herein are shown in FIG. 8, with lesion detection points predicted by the CNN shown as the x, demonstrating excellent matching with groundtruth lesion contours on T2w. .F FIG. 9 shows the FROC analysis for index lesions, clinically significant lesions, and all lesions, respectively.

As shown in FIG. 10, the example CNN implemented in accordance with the mechanisms described herein (labeled "FocalNet" in FIG. 10) achieved 90% sensitivity for index lesion at the cost of 1.02 false positives per patient, while U-Net-Sing and Deeplab triggered 54.3% and 116.8% more false detections, respectively, for the same sensitivity. Furthermore, as part (b) of FIG. 9, the example CNN implementation detected 87.9% clinically significant lesions at 1 false positive per patient, outperforming the best baseline, U-Net-Sing, by 11.1%. The partial area under the curve between 0.01 to 1 and 0.1 to 3 false positives per patient for the example CNN implementation are 0.685±0.056 and 2.570±0.101, respectively, which are higher than U-Net- Sing (0.596±0.061, 2.402±0.106). Moreover, as in part (c) of FIG. 9, the sensitivity for all PCa lesions detection is 64.4% at 1 false positive per patient, while U-Net-Sing required 1.65 false positives per patient for the same sensitivity. The example CNN implementation reached its maximum sensitivity of 89.3% at 4.64 false positives per patient, in comparison to U-Net-Sing's maximum sensitivity of 84.7% at similar false positives per patient.

Radiologist performance is shown in FIG. 9 as green cross-hair markers. Radiologists achieved 83.9% sensitivity for index lesions, 80.7% sensitivity for clinically significant lesions, and 61.8% sensitivity for all lesions, with 0.62 false positives per patient. The radiologist detection sensitivity for index lesions, clinically significant lesions, and all lesions was, respectively, 3.4%, 1.5%, and 6.2% higher than the example CNN implementation at the same false positives per patient.

FIG. 10 shows a table of example comparisons of false positives per patient produced by various techniques including techniques based on the mechanisms described herein at particular sensitivity levels.

FIG. 11 shows a table of example comparisons of false positives per patient produced by various techniques including techniques based on the mechanisms described herein at particular sensitivity levels for specific classes of lesion.

Figure 12:
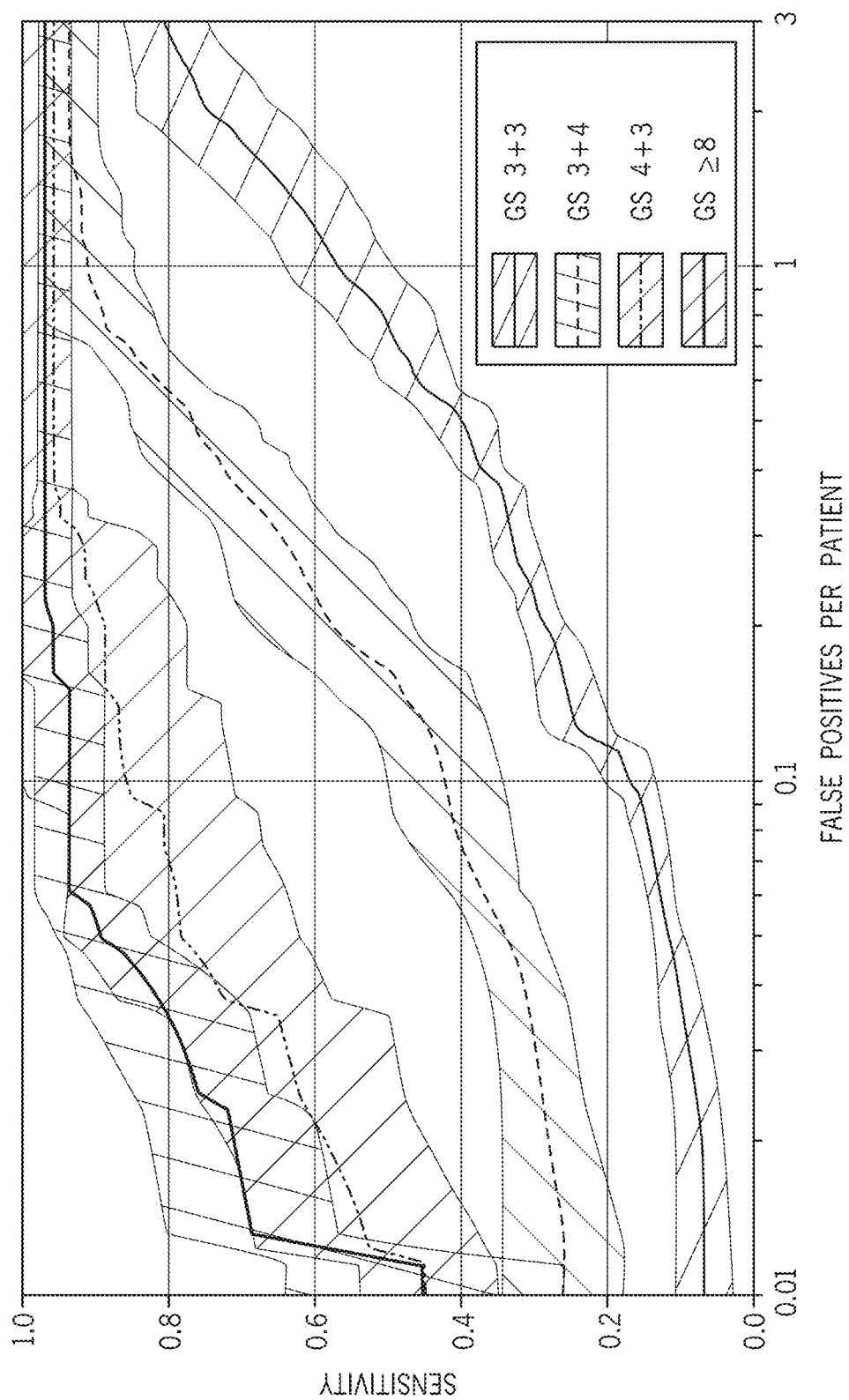
FIG. 12 shows an example of sensitivity to prostate lesions of various classes achieved by techniques based on the mechanisms described herein.

FIG. 12 shows an example of sensitivity to prostate lesions of various classes achieved by techniques based on the mechanisms described herein. Both the example CNN implemented using mechanisms described herein and baseline techniques had high sensitivity for lesions with GS≥4+3. For example, the CNN implemented using mechanisms described herein reached 95.3% and 96.8% sensitivity for GS 4+3 and GS≥8 at 0.231 and 0.377 false positives per patient, respectively. The CNN implemented using mechanisms described herein outperformed baseline techniques for the detection of GS 3+4 lesions. At 0.5 and 1 false positive per patient, the CNN implemented using mechanisms described herein respectively achieved 76.4% and 91.0% sensitivity for GS 3+4, which are 7.7% and 6.3% higher than U-Net-Sing, 15.1% and 16.9% higher than U-Net-Mult, and 16.1% and 14.3% higher than Deeplab.

Figure 13:
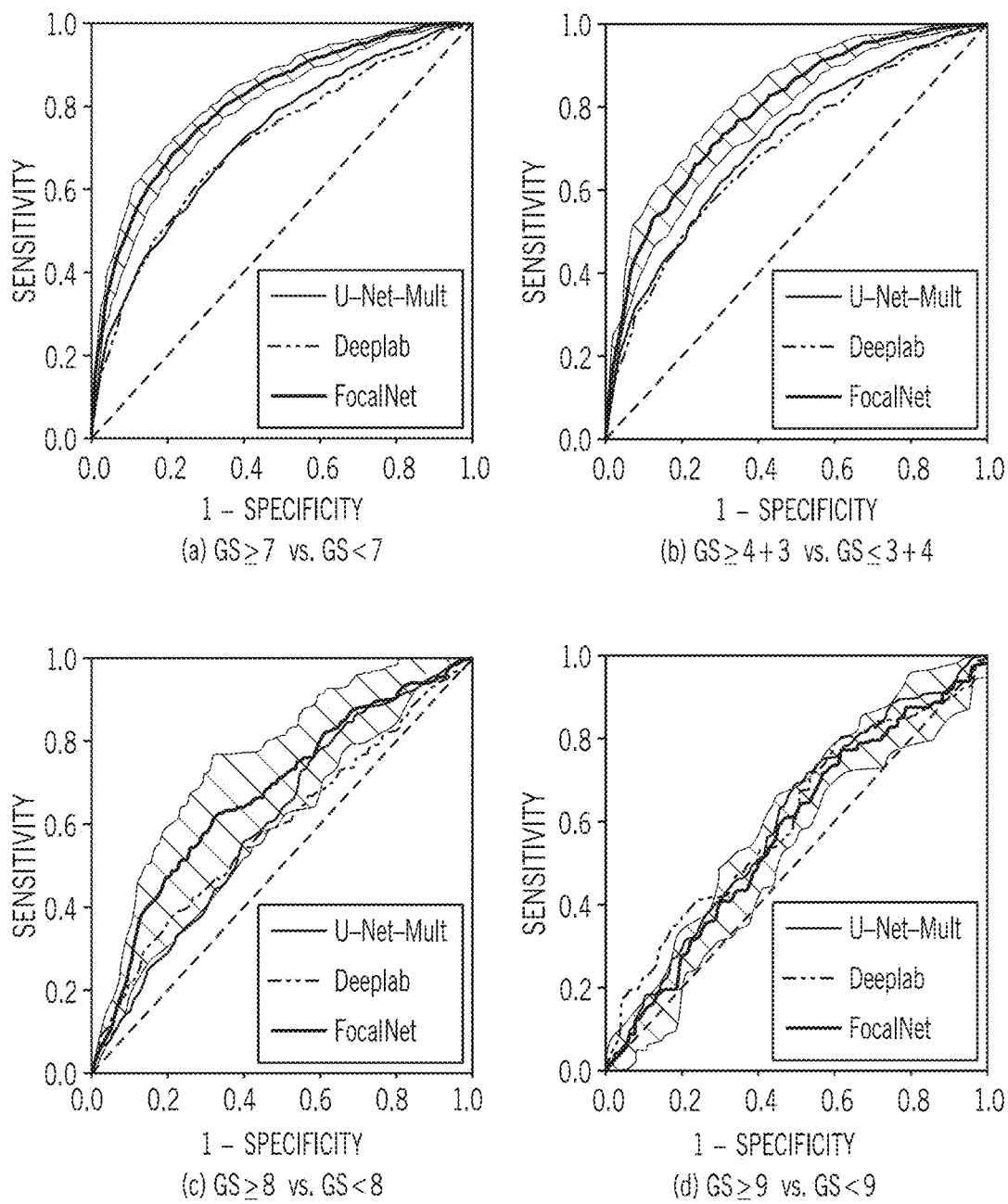
FIG. 13 shows example comparisons of sensitivity and specificity in identifying prostate lesions achieved by various techniques including techniques based on the mechanisms described herein.

FIG. 13 shows example comparisons of sensitivity and specificity in identifying prostate lesions achieved by various techniques including techniques based on the mechanisms described herein. As shown in FIG. 13, panels (a) and (b) show the ROC analysis for GS≥7 vs. GS<7 and GS>4+3 vs. GS≤3+4. The example CNN implementation achieved ROC area under the curve (AUC) 0.81±0.01 and 0.79±0.01, respectively in 5-fold cross-validation, in comparison to U-Net-Mult (0.72±0.01 and 0.71±0.03) and Deeplab (0.71±0.02 and 0.70±0.02). The example CNN implementation achieved AUC significantly higher than U-Net-Mult (p<0.0005) and Deeplab (p<0.01) for clinically significant lesion (GS≥7) classification. However, as shown in FIG. 13, panels (c) and (d), both the example CNN implementation and baseline techniques exhibited limited capabilities of classifying GS≥8 vs. GS<8 and GS≥9 vs. GS<9. The example CNN implementation has ROC AUC 0.67±0.04, and 0.57±0.02 respectively, not significantly different from U-Net-Mult (0.60±0.03, and 0.60±0.03) and Deeplab (0.59±0.01, and 0.60±0.04).

Figure 14:
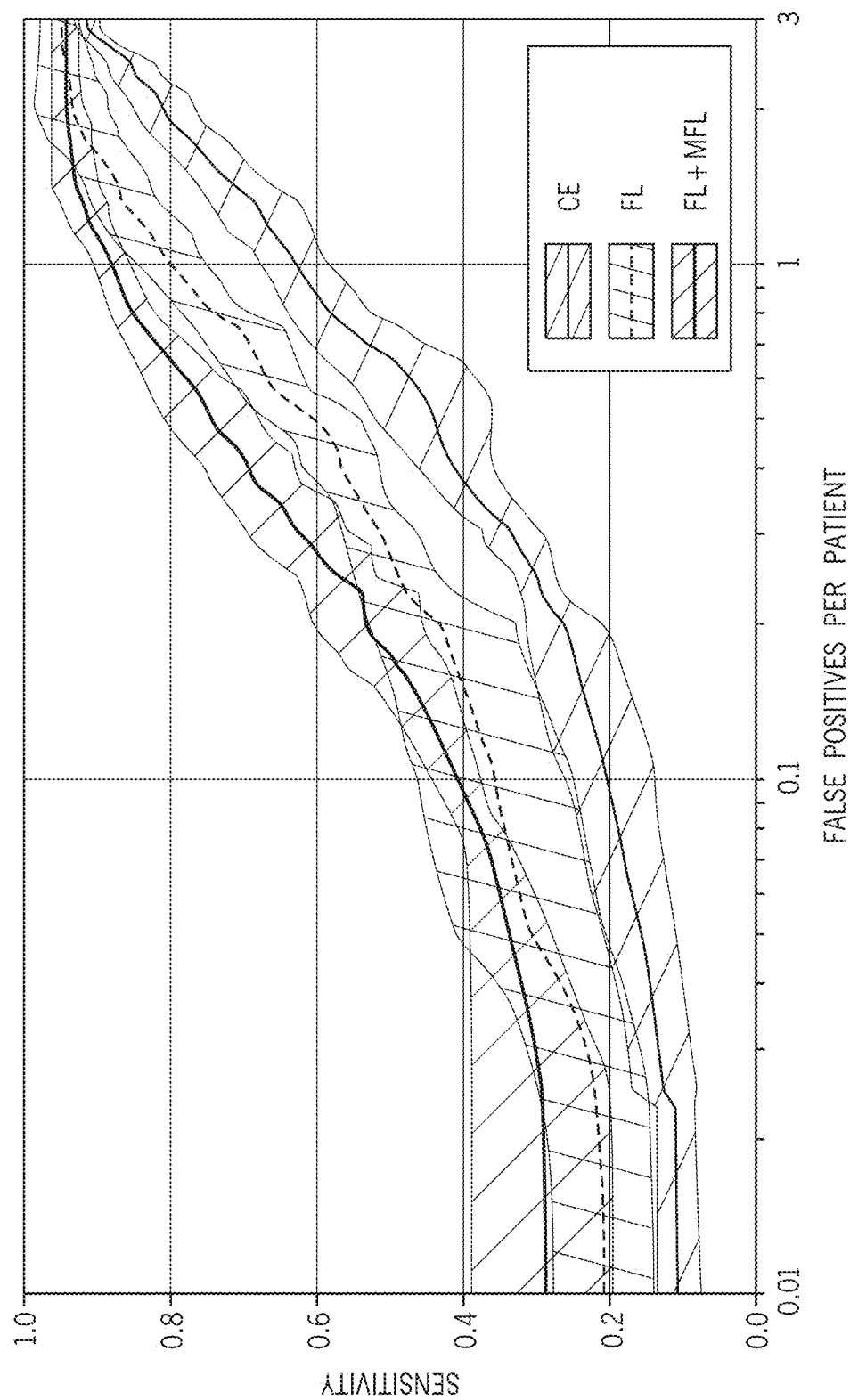
FIG. 14 shows an example comparison of sensitivity to prostate lesions achieved by various training techniques in combination with the mechanisms described herein at various false positive rates.

FIG. 14 shows an example comparison of sensitivity to prostate lesions achieved by various training techniques in combination with the mechanisms described herein at various false positive rates. The example CNN implementation was trained with different loss combinations to illustrate their contributions to PCa detection performance. Under the same setting, three different losses were compared: cross-entropy loss (CE), focal loss (FL), and the combined loss from FL and MFL (FL+MFL) described above in connection with FIG. 6A. As shown in FIG. 14, CE had only 62.9% lesion detection sensitivity at 1 false positive per patient, as the cross-entropy loss was dominated by non-cancerous pixels during the training. FL showed its effectiveness for the imbalanced labels and improved the detection sensitivity by more than 15% from CE in range of 0.05 to 1.42 false positives per patient. The combination of FL and MFL (FL+MFL) further improved the lesion detection sensitivity from CE and FL respectively by 30.3%, 14.2% at 0.5 false positives per patient and by 25.0%, 8.1% at 1 false positive per patient. Note that the detection performance of CE was marginally lower than results achieved by Deeplab, as shown in FIG. 9, which may be attributable to the ordinal encoding scheme causing the labels to become more imbalanced for CE.

Figure 15:
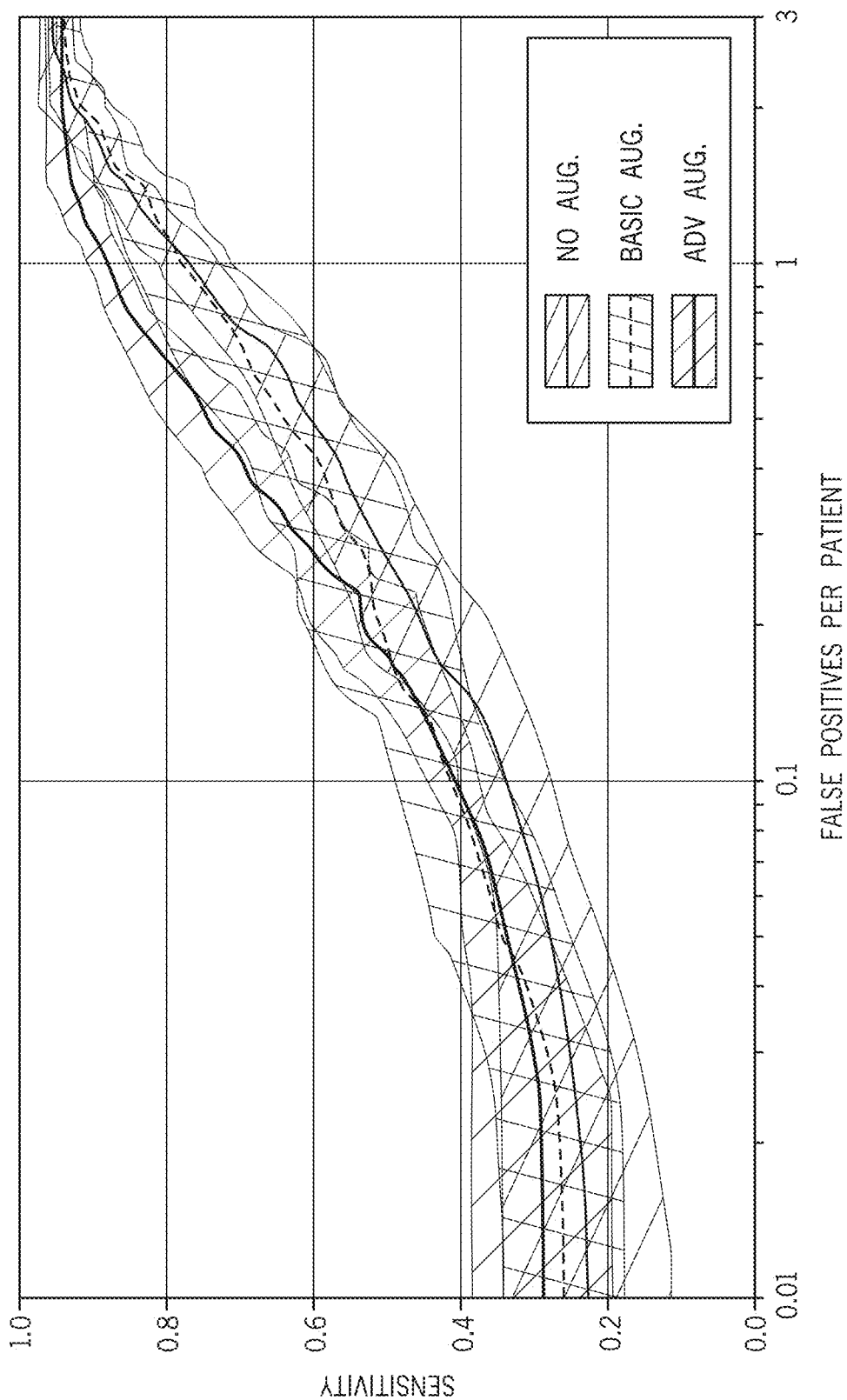
FIG. 15 shows an example comparison of sensitivity to prostate lesions achieved by various image augmentation training techniques in combination with the mechanisms described herein at various false positive rates.

FIG. 15 shows an example comparison of sensitivity to prostate lesions achieved by various image augmentation training techniques in combination with the mechanisms described herein at various false positive rates. As image augmentation is non-trivial for training a CNN when the number of training data is limited, three different augmentation strategies were compared in the context of PCa detection: training without augmentation, with basic augmentation, and with advanced augmentation. The basic augmentation included image shifting, scaling, and flipping, while the advanced augmentation additionally included intensity variation as described above in connection with FIG. 4. As shown in FIG. 15, the advanced augmentation strategy became more effective more quickly as false positives per patient become higher (>0.24), and the basic augmentation was relatively ineffective when the number of false positives per patient was greater than 0.75 as compared to no augmentation. The sensitivity with the advanced augmentation strategy was 9.8% higher than the strategy using basic augmentation at 1 false positive per patient. This suggests that applying random intensity variation during training may improve the detection of otherwise hard-to-spot lesions, rather than easy-to-spot lesions. This may be particularly relevant when there exist strong intensity variations in the original MRI data, such as variations caused by use of the endorectal coil.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

It should be understood that the above described steps of the processes of FIG. 7 can be executed or performed in any order or sequence not limited to the order and sequence shown and described in the figures. Also, some of the above steps of the processes of FIG. 7 can be executed or performed substantially simultaneously where appropriate or in parallel to reduce latency and processing times.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways.

What is claimed is:

1. A system for automatically detecting and classifying prostate lesions, the system comprising:
at least one hardware processor that is programmed to:
receive multi-parameter MRI (mp-MRI) data depicting a portion of a subject's prostate, the mp-MRI data comprising a plurality of components,
wherein a first component of the plurality of components comprises T2 weighted (T2w) data, and a second component of the plurality of components comprises apparent diffusion coefficient (ADC) data;
provide the T2w data as input to a first input channel of a plurality of input channels of a trained convolutional neural network (CNN) classification model,
wherein the trained CNN classification model is configured to receive inputs using the plurality of input channels, each of the plurality of input channels corresponding to one of the plurality of components, and provide outputs using a plurality of output channels, each of the plurality of output cannels indicating a likelihood that each pixel of the data provided to the input channels corresponds to a particular class of prostate lesion of a plurality of classes, with each class of the plurality of classes corresponding to a predicted aggressiveness of a prostate lesion in order of increasing aggressiveness, and
wherein the trained CNN classification model was trained using labeled mp-MRI data comprising a multiplicity of slices of T2w data, and a respective multiplicity of co-registered ADC data, and a combination of focal loss (FL) and mutual finding loss (MFL);
provide the ADC data as input to a second channel of the plurality of channels;
receive, from the trained CNN classification model for each of a plurality of pixels of the mp-MRI data, a plurality of output values from the respective plurality of output channels,
wherein each of the plurality of output values is indicative of a likelihood that a prostate lesion of at least the level of prostate lesion aggressiveness corresponding to that output channel is present at the pixel;
identify a prostate lesion in the mp-MRI data based one or more output values for one or more pixels of the plurality of pixels being greater than a threshold;
predict an aggressiveness of the identified prostate lesion based on which output channels had values over the threshold for the particular pixel; and
cause an indication that a prostate lesion of the predicted aggressiveness is likely present in the subject's prostate to be presented to a user.

2. A method for automatically detecting and classifying prostate lesions, the method comprising:
receiving multi-parameter MRI (mp-MRI) data depicting a portion of a subject's prostate, the mp-MRI data comprising a plurality of components,
wherein a first component of the plurality of components comprises T2 weighted (T2w) data, and a second component of the plurality of components comprises apparent diffusion coefficient (ADC) data;
providing the T2w data as input to a first input channel of a plurality of input channels of a trained convolutional neural network (CNN) classification model,
wherein the trained CNN classification model is configured to receive inputs using the plurality of input channels, each of the plurality of input channels corresponding to one of the plurality of components, and provide outputs using a plurality of output channels, each of the plurality of output cannels indicating a likelihood that each pixel of the data provided to the input channels corresponds to a particular class of prostate lesion of a plurality of classes, with each class of the plurality of classes corresponding to a predicted aggressiveness of a prostate lesion in order of increasing aggressiveness, and
wherein the trained CNN classification model was trained using labeled mp-MRI data comprising a multiplicity of slices of T2w data, and a respective multiplicity of co-registered ADC data, and a combination of focal loss (FL) and mutual finding loss (MFL);
providing the ADC data as input to a second channel of the plurality of channels;
receiving, from the trained CNN classification model for each of a plurality of pixels of the mp-MRI data, a plurality of output values from the respective plurality of output channels,
wherein each of the plurality of output values is indicative of a likelihood that a prostate lesion of at least the level of prostate lesion aggressiveness corresponding to that output channel is present at the pixel;
identifying a prostate lesion in the mp-MRI data based one or more output values for one or more pixels of the plurality of pixels being greater than a threshold;
predicting an aggressiveness of the identified prostate lesion based on which output channels had values over the threshold for the particular pixel; and
causing an indication that a prostate lesion of the predicted aggressiveness is likely present in the subject's prostate to be presented to a user.

3. A non-transitory computer readable medium containing computer executable instructions that, when executed by a processor, cause the processor to perform a method for automatically detecting and classifying prostate lesions, the method comprising:
receiving multi-parameter MRI (mp-MRI) data depicting a portion of a subject's prostate, the mp-MRI data comprising a plurality of components,
wherein a first component of the plurality of components comprises T2 weighted (T2w) data, and a second component of the plurality of components comprises apparent diffusion coefficient (ADC) data;

providing the T2w data as input to a first input channel of a plurality of input channels of a trained convolutional neural network (CNN) classification model,
   wherein the trained CNN classification model is configured to receive inputs using the plurality of input channels, each of the plurality of input channels corresponding to one of the plurality of components, and provide outputs using a plurality of output channels, each of the plurality of output cannels indicating a likelihood that each pixel of the data provided to the input channels corresponds to a particular class of prostate lesion of a plurality of classes, with each class of the plurality of classes corresponding to a predicted aggressiveness of a prostate lesion in order of increasing aggressiveness, and
   wherein the trained CNN classification model was trained using labeled mp-MRI data comprising a multiplicity of slices of T2w data, and a respective multiplicity of co-registered ADC data, and a combination of focal loss (FL) and mutual finding loss (MFL);
providing the ADC data as input to a second channel of the plurality of channels;
receiving, from the trained CNN classification model for each of a plurality of pixels of the mp-MRI data, a plurality of output values from the respective plurality of output channels,
   wherein each of the plurality of output values is indicative of a likelihood that a prostate lesion of at least the level of prostate lesion aggressiveness corresponding to that output channel is present at the pixel;
identifying a prostate lesion in the mp-MRI data based one or more output values for one or more pixels of the plurality of pixels being greater than a threshold;
predicting an aggressiveness of the identified prostate lesion based on which output channels had values over the threshold for the particular pixel; and
causing an indication that a prostate lesion of the predicted aggressiveness is likely present in the subject's prostate to be presented to a user.

4. The system of claim 1,
wherein a first output channel of the plurality of output channels is associated with a first class that corresponds to a Gleason score of 3+3,
a second output channel of the plurality of output channels is associated with a second class that corresponds to a Gleason score of 3+4,
a third output channel of the plurality of output channels is associated with a third class that corresponds to a Gleason score of 4+3,
a fourth output channel of the plurality of output channels is associated with a fourth class that corresponds to a Gleason score of 8, and
a fifth output channel of the plurality of output channels is associated with a fifth class that corresponds to a Gleason score of 9 or more.

5. The system of claim 4, wherein the CNN classification model was trained at least in part by:
(i) providing a slice of training T2w data as input to the first input channel of the untrained CNN classification model, and a slice of training ADC data corresponding to the T2w data as input to the second input channel of the untrained CNN classification model;
(ii) receiving from the untrained CNN, a first set of outputs comprising a value from each output channel for each pixel of the training mp-MRI data based on the data provided as input at (i);
(iii) generating, using label information associated with the training mp-MRI data, a plurality of binary masks that are each associated with one of the plurality of classes, each mask indicating which pixels of the training mp-MRI data are non-lesion and which pixels of the training mp-MRI data correspond to a lesion of at least the class associated with the mask;
(iv) generating a first loss value using FL based on a comparison of the plurality of masks and the first set of outputs for each pixel of the training mp-MRI data;
(v) providing the slice of training T2w data as input to the first channel of the untrained CNN classification model, and blank data as input to the second channel of the untrained CNN classification model;
(vi) receiving from the untrained CNN, a second set of outputs comprising a value from each output channel for each pixel of the training mp-MRI data based on the data provided as input at (v);
(vii) providing blank data as input to the first channel of the untrained CNN classification model, and the slide of training ADC data as input to the second channel of the untrained CNN classification model;
(viii) receiving from the untrained CNN, a third set of outputs comprising a value from each output channel for each pixel of the training mp-MRI data based on the data provided as input at (vii);
(ix) selecting, for MFL, between the second set of outputs and the third set of outputs based on which of the second set of outputs and third set of outputs more closely corresponds to the first set of outputs;
(x) generating a second loss value based on a distance between the plurality of masks and the differences between the first set of outputs and the selected set of outputs; and
(xi) repeating (i) to (x) for the multiplicity of training slices to generate the trained CNN classification model.

6. The system of claim 5,
wherein a first mask of the plurality of masks corresponds to the first class,
a second mask of the plurality of masks corresponds to the second class,
a third mask of the plurality of masks corresponds to the third class,
a fourth mask of the plurality of masks corresponds to the fourth class, and
a fifth mask of the plurality of masks corresponds to the fifth class.

7. The system of claim 1, wherein the at least one hardware processor that is programmed to:
clip the T2w data using a lower threshold corresponding to an intensity of air and an upper threshold corresponding to an intensity of bladder in the T2w data; and
normalize the clipped T2w data to a range of [0,1].

8. The system of claim 1, wherein the at least one hardware processor that is programmed to:
select a portion of the T2w data centered on the prostate depicted in the mp-MRI data; and
convert the selected portion of the T2w data to a size corresponding to an input size of the first input channel.

9. The system of claim 1, wherein the at least one hardware processor that is programmed to:
provide the T2w data as input to the first input channel of the trained CNN classification model, and blank data as input to the second channel of the trained CNN;

receive, from the trained CNN classification model for each of a plurality of pixels of the mp-MRI data, a second plurality of output values from the respective plurality of output channels;

provide blank data as input to the first input channel of the trained CNN classification model, and the ADC data as input to the second channel of the trained CNN;

receive, from the trained CNN classification model for each of a plurality of pixels of the mp-MRI data, a third plurality of output values from the respective plurality of output channels;

select one of the plurality of components, $I_{Sel}$, to segment based on which of the second plurality of output values and the third plurality of output values minimizes the expression $$I_{Sel} = \arg\min_{c \in \{I_{ADC}, I_{T2w}\}} d(\hat{y} \otimes f_{out}, \hat{y} \otimes f_c),$$

where $I_{T2w}$ is the T2w data, $I_{ADC}$ is the ADC data, $f_{out}$ and $f_c$ are the plurality of outputs and the second plurality of outputs or third plurality of outputs; and segment the selected component $I_{Sel}$ based on an inferred mask y* that minimized energy E in the expression $E(y^*) = \sum_{i=1}^{N} \phi_u(y^* | I_{ADC}, I_{T2w}) + \sum_{i<j}^{N} \phi_p(y^*_i, y^*_j | I_{Sel})$, where $\phi_u$ is the unary potential from a negative log-likelihood of a CNN predicted probability map, and $\phi_p$ is the pairwise potential from ith and jth pixels in the CNN predicted probability map.

10. The method of claim 2,
wherein a first output channel of the plurality of output channels is associated with a first class that corresponds to a Gleason score of 3+3,
a second output channel of the plurality of output channels is associated with a second class that corresponds to a Gleason score of 3+4,
a third output channel of the plurality of output channels is associated with a third class that corresponds to a Gleason score of 4+3,
a fourth output channel of the plurality of output channels is associated with a fourth class that corresponds to a Gleason score of 8, and
a fifth output channel of the plurality of output channels is associated with a fifth class that corresponds to a Gleason score of 9 or more.

11. The method of claim 10, wherein the CNN classification model was trained at least in part by:
(i) providing a slice of training T2w data as input to the first input channel of the untrained CNN classification model, and a slice of training ADC data corresponding to the T2w data as input to the second input channel of the untrained CNN classification model;
(ii) receiving from the untrained CNN, a first set of outputs comprising a value from each output channel for each pixel of the training mp-MRI data based on the data provided as input at (i);
(iii) generating, using label information associated with the training mp-MRI data, a plurality of binary masks that are each associated with one of the plurality of classes, each mask indicating which pixels of the training mp-MRI data are non-lesion and which pixels of the training mp-MRI data correspond to a lesion of at least the class associated with the mask;
(iv) generating a first loss value using FL based on a comparison of the plurality of masks and the first set of outputs for each pixel of the training mp-MRI data;
(v) providing the slice of training T2w data as input to the first channel of the untrained CNN classification model, and blank data as input to the second channel of the untrained CNN classification model;
(vi) receiving from the untrained CNN, a second set of outputs comprising a value from each output channel for each pixel of the training mp-MRI data based on the data provided as input at (v);
(vii) providing blank data as input to the first channel of the untrained CNN classification model, and the slide of training ADC data as input to the second channel of the untrained CNN classification model;
(viii) receiving from the untrained CNN, a third set of outputs comprising a value from each output channel for each pixel of the training mp-MRI data based on the data provided as input at (vii);
(ix) selecting, for MFL, between the second set of outputs and the third set of outputs based on which of the second set of outputs and third set of outputs more closely corresponds to the first set of outputs;
(x) generating a second loss value based on a distance between the plurality of masks and the differences between the first set of outputs and the selected set of outputs; and
(xi) repeating (i) to (x) for the multiplicity of training slices to generate the trained CNN classification model.

12. The method of claim 11,
wherein a first mask of the plurality of masks corresponds to the first class,
a second mask of the plurality of masks corresponds to the second class,
a third mask of the plurality of masks corresponds to the third class,
a fourth mask of the plurality of masks corresponds to the fourth class, and
a fifth mask of the plurality of masks corresponds to the fifth class.

13. The method of claim 2, further comprising:
clipping the T2w data using a lower threshold corresponding to an intensity of air and an upper threshold corresponding to an intensity of bladder in the T2w data; and
normalizing the clipped T2w data to a range of [0,1].

14. The method of claim 2, further comprising:
selecting a portion of the T2w data centered on the prostate depicted in the mp-MRI data; and
converting the selected portion of the T2w data to a size corresponding to an input size of the first input channel.

15. The method of claim 2, further comprising:
providing the T2w data as input to the first input channel of the trained CNN classification model, and blank data as input to the second channel of the trained CNN;
receiving, from the trained CNN classification model for each of a plurality of pixels of the mp-MRI data, a second plurality of output values from the respective plurality of output channels;
providing blank data as input to the first input channel of the trained CNN classification model, and the ADC data as input to the second channel of the trained CNN;
receiving, from the trained CNN classification model for each of a plurality of pixels of the mp-MRI data, a third plurality of output values from the respective plurality of output channels;

selecting one of the plurality of components, $I_{Sel}$, to segment based on which of the second plurality of output values and the third plurality of output values minimizes the expression $$I_{Sel} = \arg\min_{c \in \{I_{ADC}, I_{T2w}\}} d(\hat{y} \otimes f_{out}, \hat{y} \otimes f_c),$$

where $I_{T2w}$ is the T2w data, $I_{ADC}$ is the ADC data, $f_{out}$ and $f_c$ are the plurality of outputs and the second plurality of outputs or third plurality of outputs; and segmenting the selected component $I_{Sel}$ based on an inferred mask y* that minimized energy E in the expression $E(y^*) = \Sigma_{i=1}^{N} \phi_u(y^* | I_{ADC}, I_{T2w}) + \Sigma_{i<j}^{N} \phi_p(y^*_i, y^*_j | I_{Sel})$, where $\phi_u$ is the unary potential from a negative log-likelihood of a CNN predicted probability map, and $\phi_p$ is the pairwise potential from ith and jth pixels in the CNN predicted probability map.

16. The non-transitory computer readable medium of claim 3,
wherein a first output channel of the plurality of output channels is associated with a first class that corresponds to a Gleason score of 3+3,
a second output channel of the plurality of output channels is associated with a second class that corresponds to a Gleason score of 3+4,
a third output channel of the plurality of output channels is associated with a third class that corresponds to a Gleason score of 4+3,
a fourth output channel of the plurality of output channels is associated with a fourth class that corresponds to a Gleason score of 8, and
a fifth output channel of the plurality of output channels is associated with a fifth class that corresponds to a Gleason score of 9 or more.

17. The non-transitory computer readable medium of claim 3, wherein the CNN classification model was trained at least in part by:
(i) providing a slice of training T2w data as input to the first input channel of the untrained CNN classification model, and a slice of training ADC data corresponding to the T2w data as input to the second input channel of the untrained CNN classification model;
(ii) receiving from the untrained CNN, a first set of outputs comprising a value from each output channel for each pixel of the training mp-MRI data based on the data provided as input at (i);
(iii) generating, using label information associated with the training mp-MRI data, a plurality of binary masks that are each associated with one of the plurality of classes, each mask indicating which pixels of the training mp-MRI data are non-lesion and which pixels of the training mp-MRI data correspond to a lesion of at least the class associated with the mask;
(iv) generating a first loss value using FL based on a comparison of the plurality of masks and the first set of outputs for each pixel of the training mp-MRI data;
(v) providing the slice of training T2w data as input to the first channel of the untrained CNN classification model, and blank data as input to the second channel of the untrained CNN classification model;
(vi) receiving from the untrained CNN, a second set of outputs comprising a value from each output channel for each pixel of the training mp-MRI data based on the data provided as input at (v);
(vii) providing blank data as input to the first channel of the untrained CNN classification model, and the slide of training ADC data as input to the second channel of the untrained CNN classification model;
(viii) receiving from the untrained CNN, a third set of outputs comprising a value from each output channel for each pixel of the training mp-MRI data based on the data provided as input at (vii);
(ix) selecting, for MFL, between the second set of outputs and the third set of outputs based on which of the second set of outputs and third set of outputs more closely corresponds to the first set of outputs;
(x) generating a second loss value based on a distance between the plurality of masks and the differences between the first set of outputs and the selected set of outputs; and
(xi) repeating (i) to (x) for the multiplicity of training slices to generate the trained CNN classification model.

18. The non-transitory computer readable medium of claim 17,
wherein a first mask of the plurality of masks corresponds to the first class,
a second mask of the plurality of masks corresponds to the second class,
a third mask of the plurality of masks corresponds to the third class,
a fourth mask of the plurality of masks corresponds to the fourth class, and
a fifth mask of the plurality of masks corresponds to the fifth class.

19. The non-transitory computer readable medium of claim 3, wherein the method further comprises:
clipping the T2w data using a lower threshold corresponding to an intensity of air and an upper threshold corresponding to an intensity of bladder in the T2w data; and
normalizing the clipped T2w data to a range of [0,1].

20. The non-transitory computer readable medium of claim 3, wherein the method further comprises:
selecting a portion of the T2w data centered on the prostate depicted in the mp-MRI data; and
converting the selected portion of the T2w data to a size corresponding to an input size of the first input channel.

21. The non-transitory computer readable medium of claim 3, wherein the method further comprises:
providing the T2w data as input to the first input channel of the trained CNN classification model, and blank data as input to the second channel of the trained CNN;
receiving, from the trained CNN classification model for each of a plurality of pixels of the mp-MRI data, a second plurality of output values from the respective plurality of output channels;
providing blank data as input to the first input channel of the trained CNN classification model, and the ADC data as input to the second channel of the trained CNN;
receiving, from the trained CNN classification model for each of a plurality of pixels of the mp-MRI data, a third plurality of output values from the respective plurality of output channels;
selecting one of the plurality of components, $I_{Sel}$, to segment based on which of the second plurality of output values and the third plurality of output values minimizes the expression $$I_{Sel} = \arg\min_{c \in \{I_{ADC}, I_{T2w}\}} d(\hat{y} \otimes f_{out}, \hat{y} \otimes f_c),$$

where $I_{T2w}$ is the T2w data, $I_{ADC}$ is the ADC data, $f_{out}$ and $f_c$ are the plurality of outputs and the second plurality of outputs or third plurality of outputs; and segmenting the selected component $I_{Sel}$ based on an inferred mask y* that minimized energy E in the expression $E(y^*)=\Sigma_{i=1}^{N}\phi_u(y^*|I_{ADC},I_{T2w})+\Sigma_{i<j}^{N}\phi_p(y^*_i, y^*_j|I_{Sel})$, where $\phi_u$ is the unary potential from a negative log-likelihood of a CNN predicted probability map, and $\phi_p$ is the pairwise potential from ith and jth pixels in the CNN predicted probability map.

22. A system for determining a class of a cancer, the system comprising:

at least one hardware processor that is programmed to:
receive multi-parameter imaging data depicting a portion of a subject:
provide a first subset of the multi-parameter imaging data as input to a first channel of a trained convolutional neural network (CNN);
provide a second subset of the multi-parameter imaging data as input to a second channel of the trained CNN;
receive, from the trained CNN, a set of output values corresponding to a set of output channels for a plurality of pixels of the multi-parameter imaging data, the set of output channels corresponding to a set of classes of cancer in order of increasing aggressiveness, and each value indicating a likelihood that the pixel depicts cancerous tissue of at least a particular class of cancer corresponding to the output channel from which the value was output;
identify a cancer region in the multi-parameter imaging data based on one or more output values for one or more pixels corresponding to the cancer region being greater than a threshold;
predict an aggressiveness of the identified cancer region based on which of the output channels had values over the threshold for one or more pixels; and
generate a report indicating that the predicted aggressiveness is present in the cancer region.

* * * * *